(12) United States Patent
Foung et al.

(10) Patent No.: US 6,692,908 B1
(45) Date of Patent: Feb. 17, 2004

(54) PREVENTION AND TREATMENT OF HCV INFECTION EMPLOYING ANTIBODIES THAT INHIBIT THE INTERACTION OF HCV VIRIONS WITH THEIR RECEPTOR

(75) Inventors: Steven K. H. Foung, Stanford, CA (US); Kenneth G. Hadlock, San Francisco, CA (US)

(73) Assignee: Stanford University, Palo Alto, CA (US)

( * ) Notice: Subject to any disclaimer, the term of this patent is extended or adjusted under 35 U.S.C. 154(b) by 0 days.

(21) Appl. No.: 09/430,489

(22) Filed: Oct. 29, 1999

Related U.S. Application Data

(63) Continuation-in-part of application No. 09/187,057, filed on Nov. 5, 1998, now abandoned.

(51) Int. Cl.$^7$ ............................ C12Q 1/70; C12N 5/12; C07K 16/10
(52) U.S. Cl. .................. 435/5; 435/339; 530/388.3
(58) Field of Search .................. 435/5, 339; 530/388.3

(56) References Cited

U.S. PATENT DOCUMENTS

| 5,514,539 A | 5/1996 | Bukh et al. ................. 435/5 |
| 5,695,390 A | 12/1997 | Mizuno et al. ............. 451/124 |
| 6,538,114 B1 * | 3/2003 | Persson et al. ........... 530/388.3 |

FOREIGN PATENT DOCUMENTS

| WO | WO 97/40176 | 10/1997 |
| WO | WO 99/24054 | 11/1998 |
| WO | WO 00/26418 | 10/1999 |

OTHER PUBLICATIONS

Habersetzer et al., Isolation of human monoclonal antibodies (HMabs) directed at conformational determinants of the hepatitis C virus (HCV) E2 envelope proteins. Hepatology, Supplement, vol. 24, No. 4, part 2, Oct. 1996, p. 381A, Abstract No. 1020.*
International Search Report issued for corresponding PCT application PCT/US01/45029.
Chan, S–W. et al., "Human recombinant antibodies specific for hepatitls C virus core and envelope E2 peptides from an immune phage display library", Journal of General Virology, 77:251–2539, 1996.
Database EMBL Online retrieved from EBL Database accession No. Q81497, XP002222487 abstract.
Hadlock, K.G. et al, Human Monoclonal Antibodies That Inhibit Binding Of Hepatitis C Virus E2 Protein to CD81 and Recognize Conserved Conformational Epitopes, *J. Virology*, 74:10407–10416, 2000.
Prince, A. et al., Visualization of hepatitis C virions and putative defective interfering particles isolated from low–density lipoproteins, *Journal of Viral Hepatitis*, 3:11–17, 1996.

da Silva Cardosa et al (1998) *J. of Med. Virology* 55, 28–34.
DeLalla et al (1993) *J. Hepatol. 18*, 163–167.
Deleersnyder et al (1997) *J. of Virology 71*, 697–704.
Foung et al (1990) *J. Immunol. Methods 70I*, 83–90.
Habersetzer et al (1998) *Virology 249*, 32–41.
Hadlock et al (1997) *J. of Virology 71*, 5828–5840.
Lanford et al (1993) *Virology 197*, 225–235.
Mahaney et al (1994) *Hepatology 20*, 1405–1411.
Meola et al (1995) *J. Immunol. 154*, 3162–3172.
Mondelli et al (1994) *J. Virol. 68*, 4829–4836.
Moradpour et al (1996) *J. Med. Virol. 48*, 234–241.
Plaisant et al (1997) *Res. Virol.* 148–169.
Puntoriero et al (1998) *EMBO J. 17*, 3521–3533.
Ralston et al (1993) *J. of Virology 67*, 6753–6761.
Rosa et al (1996) *PNAS USA 93*, 1759–1763.
Siemoneit et al (1994) *Hybridoma 13*, 9–13.
Simmonds (1995) *Hepatology 21*, 570–583.
Tafi et al (1997) *Biol. Chem. 378*, 495–502.
Ward et al (1995) *PNAS USA 92*, 6773–6777.
Zimmerman et al (1990) *J. Immunol. Methods 134*, 43–50.
Siemoneit, K. et al. (1995) *Clin. and Experimental Immun. 101*, 278–83.
Abrignani (1997) *Springer Semin. Immunopathology 19*, 47–55.
Akatsuka et al (1993) *Hepatology 18*, 503–510.
Barbas and Burton (1994) *Cold Spring Harbor Laboratory Course Manual: Monoclonal Antibodies from Combinatorial Libraries.*
Burioni et al (1998) *Hepatology 28*, 810–814.
Burton and Barbas et al (1994) *Advances in Immunology 57, Vi+391p.*, 191–280.

* cited by examiner

Primary Examiner—Donna C. Wortman
(74) Attorney, Agent, or Firm—Choate, Hall & Stewart

(57) ABSTRACT

Human monoclonal antibodies binding to epitopes common to type 1 and 2 HCV are provided, as well as conformationally conserved HCV E2 2a and 2b proteins. Compositions comprising the antibodies find use in diagnosis and therapy. The antibodies recognize conformational epitopes that are conserved across multiple genotypes of HCV. Thus the antibodies have the potential to be useful in the prevention and treatment of the majority of HCV infections. A subset of the antibodies (CBH-2, CBH-5, CBH-7, CBH-8C, CBH-8E, and CBH-11) have the ability to prevent the binding of HCV E2 proteins of multiple genotypes to human CD81, a possible co-receptor for HCV infection. A subset of the antibodies (CBH-2 and CBH-5) have been shown to inhibit the binding of HCV virions (as opposed to purified E2 protein) to human CD81. A further subset of the antibodies (CBH-4D, CBH4B, CBH-8C, and CBH-9) have been shown to prevent HCV envelope mediated fusion using an HCV psuedotype system.

9 Claims, 19 Drawing Sheets

(11 of 19 Drawing Sheet(s) Filed in Color)

Sequence of central fragment for HCV E2 vaccinia constructs Q1a, Q1b, Q2a, & Q2b compared to representative sequences of the appropriate HCV genotypes. Accession numbers for the representative sequences of each genotype are as follows HCV 1A = M62321, HCV 1B = D10750, HCV 2A = D00944, HCV 2B = D10988. Phlyogenetic analysis performed with CLUSTALV and DNAPARS program of the PHYLIP package.

Sequences amplified from central region of HCV E2 vaccinia virus clones

```
>hcv-1a3, (Q1a)
    CTCAACTGGATTCACCAAAGTGTGCGGAGCGCCCCCCTGTGTCATCGGAGGGGCGGG
CAACAACACCTT        GCGCTGCCCCACTGATTGTTTCCGCAAGCATCCGGAAGCCAC
GTACTCTCGGTGCGGCTCCGGTCCCTGGATTACGCCCAGGTGCCTGGTc >hcv-1b8, (Q1b)
    TGGCACAGGGTTCACCAAGACGTGTGGGGCCCCCCCATGTAACATCGGGGGGGTCGG
CAATAACACCTT        GACTTGCCCCACGGACTGTTTCCGGAAGCACCCCGAGGCCAC
TTACACCAAATGTGGTTCGGGGCCTTGGCTGACACCTAGGTGCATAGTt >hcv-2a-25, (Q2a)
CTCCACTGT TTCACCAAAACTTGCGGCGCACCACCCTGCCGCATCAGAGCTGACTT
TAATGCCAGCACggaCCTGCTGTGCCCCACGGACTGTTTCAGGAAGCATCCTGAAGCCAC
TTACATCAAATGTGGCTCTGGGCCCctgtgacgccaaagtgcctgata >HCV-2B-1, (Q2b)
TGGGACTGGGTTCACTAAGACATGCGGTGCACCACCTTGCCGCATTAGGAGGGACTG
CAACGGAACCCTcgaCCTATTGTGCCCCACAGACTGTTTCAGAAAGCACCCAGATACTAC
CTACCTTAAGTGTGGAGCGGGGCCTTGGTTGACCCCCAAATGCATGGTa
```

Figure 2

| Name | Sequences |
|---|---|
| HCV-1a    | CTCAACTGGA TTCACCAAAG TGTGCGGAGC GCCTCCTTGT GTCATCGGAG GGGCGGGCAA |
| HCV-Q1a-FR | .......... .......... .......... ...C..C... .......... .......... |
| HCV-1b    | TAGT.....G .....T..GA C........G C..C..G... AA......G. ...TC..T.. |
| HCV-Q1b-FR | TGGC..A..G ........GA C...T..G.. C..C..A... AA......G. ...TC..... |
| HCV-2a    | ...C.....C .A......GA CT.....C.. A..A..C..C CG...TA... CT.ACTT... |
| HCV-Q2a-FR | ...C....-T .........A CT.....C.. A..A..C..C CG....A... CT.ACTTT.. |
| HCV-2b    | .GGG.....G .....T..GA CA.....T.. A..A.....C CG...TA.GA AA.ACTA... |
| HCV-Q2b-FR | TGGG.....G .....T..GA CA.....T.. A..A.....C CG...TA.GA ...ACT.... |
| | |
| HCV-1a    | CAACACC--- ---CTGCACT GCCCCACTGA TTGCTTCCGC AAGCATCCGG ACGCCACATA |
| HCV-Q1a-FR | .......... ...T...G.. .......... ...T...... .......... .A.....G.. |
| HCV-1b    | .CG....... ...T..AT.. .......G.. C........G .....C..C. .G..T..T.. |
| HCV-Q1b-FR | T......... ...T..ACT. .......G.. C..T.....G .....C..C. .G.....T.. |
| HCV-2a    | TGC..G.ATG GACT..TTG. .......G.. C..T..TA.G .........T .TA....C.. |
| HCV-Q2a-FR | TGC..G.ACG GAC....TG. .......G.. C..T...A.G .........T .A.....T.. |
| HCV-2b    | ..G...TATC GATT.ATTG. .......A.. C..T..TA.G .....C..A. .T..T..C.. |
| HCV-Q2b-FR | .GGA...CTC GAC..ATTG. .......A.. C..T...A.A .....C..A. .TA.T..C.. |
| | |
| HCV-1a    | CTCTCGGTGC GGCTCCGGTC CCTGGATCAC ACCCAGGTGC CTGGTC |
| HCV-Q1a-FR | .......... .......... .......T.. G......... ...... |
| HCV-1b    | .A.AAAA..T .....G..G. .....T.G.. ...T...... ..A..A |
| HCV-Q1b-FR | .A.CAAA..T ..T..G..G. .T...C.G.. ...T...... A.A..T |
| HCV-2a    | .ATCAAA..T .....T..G. .....C.... G..A...... ...A.. |
| HCV-Q2a-FR | .ATCAAA..T .....T..G. ..CT.-.G.. G..A.A.... ...A.A |
| HCV-2b    | TCT.AA...T ..AG.A..G. .T...T.A.. T......... .....A |
| HCV-Q2b-FR | .CT.AA...T ..AG.G..G. .T...T.G.. C....AA... A....A |

One most parsimonious tree found:

```
                   +--HCV-2B-1.C
          +-----7
          !       +--hcv-2B,
     +-----6
     !    !       +--hcv-2a-25.
     !    +-----5
  +--4            +--HCV-2A,
  !  !
  !  !            +--hcv-1b8.se
+--2 +----------3
!  !             +--HCV-1B,
--1 !
   ! +-----------------HCV-Q1a
```

Figure 3

Figure 5. Reactivity obtained with 12 HCV 2b Sera

PREVENTION AND TREATMENT OF HCV INFECTION EMPLOYING ANTIBODIES THAT INHIBIT THE INTERACTION OF HCV VIRIONS WITH THEIR RECEPTOR

CROSS REFERENCE TO RELATED APPLICATIONS

This application is a continuation in part of U.S. Ser. No. 09/187,057 filed Nov. 5, 1998, abandoned which disclosure is hereby incorporated by reference.

GOVERNMENT LICENSE RIGHTS

The U.S. government has a paid-up license in this invention and the right in limited circumstances to require the patent owner to license others on reasonable terms as provided for by the terms of grant No. DA60596 and HL33811 awarded by the National Institutes of Health (NIH).

INTRODUCTION

1. Technical Field

The field of this invention is related to the preparation of human monoclonal. antibodies (HMab) to structurally conserved epitopes of HCV found in a high proportion of patients for diagnosis and therapy and the ability to distinguish genotype by the use of antibodies.

2. Background

Hepatitis C virus (HCV) is an enveloped virus the genetic information for which is encoded in a 9.5 kb positive strand RNA genome. A highly conserved noncoding region of 341 bp is localized at the 5'-end of this viral genome, which is followed by a long open-reading frame coding for a polyprotein of approximately 3,010 amino acids. Two putative envelope glycoproteins E1 (gp35) and E2 (gp72) have been identified with 5 or 6 and 11 N-linked glycosylation sites, respectively. A high level of genetic variability is associated with the envelope genes. This is highly accentuated at the 5'-end of the E2 gene, where two hypervariable regions termed HVR1 and HVR2, have been described. Antibodies to HVR1 appear to mediate virus neutralization in cell culture and chimpanzee protection studies (Farci, et al., 1996 *Proc Natl Acad Sci USA*. 93:15394–15399; Shimizu, et al., 1994 *J Virol*. 68:1494–1500). Unfortunately, antibodies to HVR1 tend to be isolate specific and over time drive the replication of new viral variants that the existing immune response does not recognize (Farci, et al, 1994 *Proc Natl Acad Sci USA*. 91:7792–7796; Weiner, et al., 1992 *Proc Natl Acad Sci USA*. 89:3468–3472; Kato, et al., 1993 *J Virol*. 67:3923–3930), although progress has been made at inducing a broader immune response to HVR1 related sequences (Puntoriero, et al., 1998 *EMBO Journal* 17:3521–3533). HCV envelope antigens appear to be highly immunogenic when expressed in glycosylated forms (da Silva Cardoso, et al., 1997 *Ann. Hematol*. 74:135–7). Preliminary data suggest the existence of conserved epitopes within the E2 protein (Lesniewski, et al., 1995 *J. Med. Virol*. 45:415–22). The existence of neutralizing antibodies in serum from infected patients has been proposed.

Studies using HCV E1-E2 proteins expressed in mammalian cells showed that infected individuals have an antibody response to HCV E2 composed in part to epitopes that are conformational in nature (Harada, et al., 1994 *J Gen. Virol*. 76:1223–1231). Studies involving the isolation of human monoclonal or recombinant antibodies to HCV E2 protein showed that a substantial fraction of these antibodies recognize conformational epitopes (da Silva Cardoso et al., 1998 *J. Med Virol*. 55:28–34; Burioni et al., 1998 Hepatology 28:810–814; Habersetzer et al., (1998) *Virology* 249:32–41). As to biological function of these domains, investigators have employed surrogate assays to provide insights into virus neutralization since the virus cannot be grown, in vitro (Houghton. Hepatitis C viruses. In Fields B N, Knipe D M, Howley P M (eds) *Virology*. Lippincott-Raven, Philadelphia, pp 1035–1058). One surrogate assay, the neutralization of binding (NOB) assay, evaluates the ability of a given antibody or serum to prevent the association of HCV E2 protein with a human T-cell line (Rosa, et al., 1996 *Proc Natl Acad Sci USA*. 93:1759–1763). The finding that serum antibodies obtained from chimpanzees protected by vaccination were strongly positive in the NOB assay provides support for the relevance of the assay as a measure of virus neutralization activity (Rosa, et al., supra; Ishii, et al., 1998 *Hepatology* 28:1117–1120).

The human tetraspannin cell surface protein CD81 (TAPA-1, for review see Levy, et al., 1998 *Ann. Rev. Immunol*. 16:89–109) is the target protein bound by HCV E2 in the NOB assay (Pileri, et al., 1998 *Science*. 282:938–941). Furthermore, human CD81 binds to free virions, and subsequently is a possible receptor for HCV (Pileri, et al., supra). Using HCV 1a E2 proteins, several human monoclonal antibodies to HCV E2 protein have been reported to inhibit the interaction of HCV E2 with human cells (Burioni, et al., 1998 *Hepatology* 28:810–814; Habersetzer, et al., 1998 *Virology* 249:32–41). However, little is known about the conservation of the epitopes recognized by the NOB positive antibodies in HCV E2 proteins of different genotypes.

Other approaches to detection of and protection against HCV include the development of peptide mimetics. As an example, peptide mimetics of Hepatitis type A and C viral proteins have been created through production of randomly generated synthetic and phage-display peptide libraries for use in detection assays and vaccination therapies (Mattioli, et al., 1995 *J Virology* 69:5294–5299 and Prezzi, et al., 1996 *J Immunol*. 156:4504–4513). However, effective antibody binding of these mimotopes has only been compared to linearly defined viral epitopes. The sequential recombinant fusing of several linearly defined immunodominant HCV epitopes has been described for use in diagnostic assays (Chein, et al., 1999 *J Clin Microbiol*. 37:1393–1397). However, this multiple-epitope fusion antigen designed from linear epitopes was not created to function in the same capacity as a conformational mimetic: it was not designed to interfere with binding to a target receptor.

It is therefore of substantial interest to identify neutralizing antibodies in serum from infected patients which may be used in diagnosis and passive immunotherapy, where the antibodies would originate from a human cell, and provide for neutralization of a broad spectrum of genotypes, particularly in a particular geographical area. Both breadth of reactivity to multiple HCV genotypes and the ability to interfere with the binding of HCV virions to susceptible cells would be key attributes for a therapeutically useful neutralizing antibody. Also of interest is the design of peptide and non-peptide (inorganic) structural mimetics of HCV envelope proteins.

Relevant Literature

References providing background information concerning HCV include Abrignani 1997 Springer *Semin. Immunopathology* 19:47–55; Simmonds, 1995 *Hepatology* 21:570–583; and Mahaney et al., 1994 *Hepatology* 20:1405–1411.

da Silva Cardosa et al., 1998 *J. of Med. Virology* 55:28–34 describe human monoclonal antibodies to HCV E1/E2. Habersetzer et al., 1998 *Virology* 249:32–41 describe human monoclonal antibodies capable of recognizing HCV E2 genotypes 1a and 1b. Burioni et al., 1998 report human recombinant Fabs for the HCV E2 protein. Deleersnyder et al., 1997 *J. of Virology* 71:697–704 describe an E2 reactive monoclonal antibody. Other references related to the use of antibodies to HCV include Burioni et al., 1998 *Hepatology* 28:810–814; Akatsuka, et al., 1993 *Hepatology* 18:503–510; DeLalla, et al., 1993 *J. Hepatol.* 18:163–167; Mondelli, et al., 1994 *J. Virol.* 68:4829–4836; Siemoneit, et al., 1994 *Hybridoma* 13:9–13; and Moradpour, et al., 1996 *J. Med. Virol.* 48:234–241; for producing human antibodies, Foung, et al., 1990 *J. Immunol. Methods* 70:83–90; Zimmerman, et al., 1990 *J. Immunol. Methods* 134:43–50;for producing modified antibodies using combinatorial libraries, Burton and Barbas, Dixon, F J (Ed.) *Advances in Immunology*, Vol. 57, Vi+391 p. *Academic Press, Inc.,* San Diego, Calif. 191–280, 1994; Plaisant, et al., 1997 *Res. Virol.* 148–169; and Barbas and Burton, *Monoclonal Antibodies from Combinatorial Libraries. Cold Spring Harbor Laboratory Course Manual,* Cold Spring Harbor, N.Y., 1994.

An assay for antibodies binding to HCV E2 is described by Rosa, et al., 1996 *Proc Natl Acad Sci USA* 93:1759–1763.

Vaccinia virus or baculovirus constructs having a portion of the HCV genome are described by Ralston et al., 1993 *J. of Virology* 67:6733–6761 and Lanford et al., 1993 *Virology* 197:225–235.

SUMMARY OF THE INVENTION

Monoclonal antibodies, including human monoclonal antibodies, are provided which bind to the dominant HCV types in major geographical areas. Specifically, a family of monoclonal antibodies binding to conformationally conserved epitopes of the HCV E2 protein are provided. Among the family are antibodies which bind to the dominant genotypes found in the United States, so as to be substantially pan-monoclonal antibodies in being able to bind to almost all cases of HCV infection which have been diagnosed in the United States, as well as at least a substantial proportion of the cases in other geographic locales. The monoclonal antibodies find use in a variety of diagnostic assays. In addition, conformationally conserved expression of recombinant type 1 and type 2 HCV E2 proteins are provided for use in assays, screening drugs and for other purposes. The human antibodies find use in passive immunotherapy strategies for reducing viral load of infected individuals and interfering with infection of target cells. Antibodies recognizing conformationally dependent epitopes can also be used to provide a template for the rational design of peptide and inorganic conformationally-defined epitope mimetics.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2 (SEQ ID NOS: 9–12) describes sequences amplified from the central region of the HCV E2 vaccinia virus clones. Shown are the sequences of the central fragment for HCV E2 vaccinia constructs Q1a, Q1b, Q2a, & Q2b as compared to representative sequences of the appropriate HCV genotypes. Accession numbers for the representative sequences of each genotype are as follows HCV 1A=M62321, HCV 1B=D10750, HCV2A=D00944, HCV 2B=D10988. Phylogenetic analysis was performed with CLUSTALV and DNAPARS program of the PHYLIP package.

FIG. 3 (SEQ ID NOS: 1–8) is a comparison of sequences of HCV: -1a, Q1a-FR, -1b, -Q1b-FR, -2a, Q2a-FR, -2b, -Q2b-FR, using the most parsimonious tree found.

FIG. 4 shows graphs of the reactivity of HCV sera with HCV E2 proteins of different genotypes. HCV E2 protein expressed by $6\times10^5$ HeLa cells infected with vaccinia virus Q1a ■, Q1b ▲, Q2a ▼, Q2b ♦, or non recombinant vaccinia virus VWA ○was captured onto wells coated with 500 ng of GNA lectin. Wells were washed and blocked and bound protein was incubated with increasing dilutions (x axis) of genotyped HCV sera or an HCV negative serum (indicated above the graph). Values are the mean absorbence of replicate wells. Error bars indicate one standard deviation from the mean.

FIG. 5 is a bar graph indicating the reactivity of sera from individuals infected with HCV genotype 2b with HCV E2 proteins of multiple genotypes. Twelve sera from individuals infected with HCV genotype 2b (x axis) were titrated against HCV E2 proteins of genotypes 1a (dark blue bars), 1b (magenta bars), 2a (yellow bars), and 2b (light blue bars). The dilution of the serum that resulted in a mean specific absorbence (mean absorbence obtained with HCV E2 containing extract subtracted from the mean specific absorbence obtained with the VWA extract) of 0.5 is indicated on the y axis. This value was calculated from titration curve data analogous to that presented in FIG. 4.

FIG. 6 depicts a schematic of a direct binding assay to assess for antibodies that recognize conformational epitopes of HCV E2 envelope proteins employed in the experiments described in FIGS. 7, 8, and 9. GNA lectin is coated onto a solid surface and then added E2-containing protein extracts are captured by the lectin. Test antibodies are allowed to bind to the captured E2, the excess unbound is removed, and bound antibody is detected with a labeled secondary antibody.

FIG. 7 is a bar graph of the reactivity of HCV HMAbs to HCV E2 captured by lectins. Proteins from cytoplasmic extracts of $6\times10^5$ cells infected with wild type (Bars labeled VWA) or HCV 1a E2 (HCV 1a) (bars labeled HCV) expressing vaccinia virus were applied to microtiter plates coated with 500 ng of *Galanthus nivalis* (GNA) or *Tiriticum vulgaris* (WGA). Captured proteins were incubated with 5 $\mu$g/ml of the indicated HMAbs (x axis). R04 is an isotype-matched control. Bound HMAb was detected with anti-human antibody-alkaline phosphatase and appropriate substrate. Bars indicate the mean OD value of replicate wells. Error bars indicate 1 standard deviation from the mean.

FIG. 8 shows graphs of HCV antibody reactivity with E2 protein of divergent HCV genotypes. HCV E2 proteins expressed by $6\times10^5$ HeLa cells infected with vaccinia virus Q1a ■, Q1b ▲, Q2a ▼, or Q2b ♦ was captured onto wells coated with 500 ng of GNA lectin. Wells were washed and blocked and bound protein was incubated with the indicated HCV HMAbs (HMAb identified above each of FIGS. 9A–9J) and control HMAb (R04) FIG. 9K to a CMV protein (Ward, et al., 1995, *Proc Natl Acad Sci USA.* 92:6773–6777). Values are the mean specific binding (extracts of cells infected with vaccinia virus expressing HCV E2 protein—wt vaccinia extracts) of replicate wells. Reactivity of HCV and control HMAbs with proteins from wt vaccinia virus infected cells did not exceed an absorbence of 0.04. Error bars indicate one standard deviation from the mean.

DETAILED DESCRIPTION OF THE INVENTION

Figure 1:
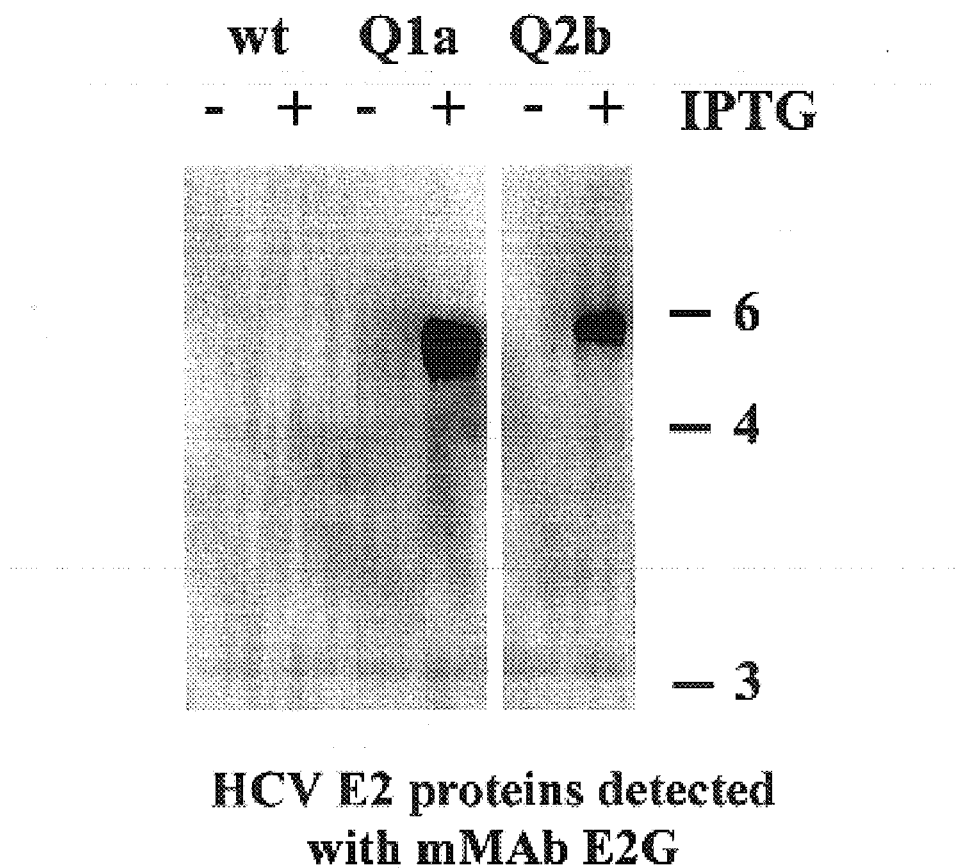
FIG. 1 is a Western blot indicating the expression of HCV E2 proteins by some of the vaccinia virus constructs described in this application. Cytoplasmic extracts were prepared from CV1 cells infected with wild type vaccinia virus and then transfected with pVOTE (wt) or recombinant pVOTE expressing HCV E2 of genotype 1a (Q1a) or 2b (Q2b). Cells were cultured for 24 hours in the presence (+) or absence (−) of the inducer IPTG. Extract corresponding to $2 \times 10^5$ cells was fractionated by SDS PAGE and blotted onto nitrocellulose. HCV E2 protein was revealed by incubation with 1/500 diluted ascites fluid of mMab E2G using the ECL detection system (Amersham). Migration of molecular weight standards is indicated at right.

Monoclonal antibodies, particularly human monoclonal antibodies ("HMAbs"), are provided which bind to one or more hepatitis C virus genotypes, which antibodies find use for diagnosis and therapy. A panel of human monoclonal antibodies (HMAbs) from peripheral B-cells of an individual with asymptomatic HCV infection and having a high serum neutralization of binding titer were produced and characterized. Eleven HMAbs to HCV E2 have been produced. One group of antibodies binds to the genotypes of HCV types 1 and 2, while other antibodies bind to fewer than this group of genotypes. HCV types 1 and 2 together are the dominant virus types encountered in the western hemisphere and other geographic locations. The antibodies bind to conformational epitopes which are conserved across virus types and genotypes. The antibodies bind to HCV E2 proteins of genotypes 1a, 1b, 2a, and 2b and a subset of these antibodies inhibit the interaction of these E2 proteins with human CD81. By virtue of the variety of binding profiles of the antibodies, diagnostic assays may be employed which will detect a plurality of types and genotypes, so as to provide a pan-anti-HCV antibody for HCV encountered in the United States, while at the same time being able to dissect individual genotypes by subtractive analysis. In addition, the antibodies being human, they may be used for passive immunization, as protective therapy for individuals at risk for HCV or as a therapy for people who are seropositive for HCV.

The HMAbs of the invention offer several advantages over existing HMAbs against HCV. Because non-homologous primary amino acid sequences may still define immunologically identical tridimensional protein structures, HMAbs binding to structurally conserved epitopes can recognize multiple, sequentially divergent HCV genotypes in native conformation, whereas antibodies recognizing only linear or denatured epitopes may not. In particular, conformationally dependent anti-HCV E2 HMAbs may effectively interfere with the interaction of native HCV virus and its cellular target receptors. Using conformationally dependent HMAbs to actively interfere with the ability of native HCV virus to bind to target cell receptors such as CD81 has specific therapeutic application for reducing viral load in infected individuals, and preventing infection or re-infection of organs in non-infected individuals, particularly in recent organ transplant recipients. Certain subsets of the HMAbs interfere with E2-associated viral infection by mechanisms other than preventing direct interaction with CD81. This subset of antibodies interferes with viral infectivity by a number of possible mechanisms, including preventing E2 binding to co-receptor proteins, conformational changes in E1 and/or E2 proteins necessary for target cell binding, E1 and E2-mediated viral fusion to target cells, and uncoating of HCV virions. Because they bind distinct conformational epitopes, the subset of HMAbs that directly interferes with E2 binding to CD81 complements HMAbs in the subset that interfere with infectivity by other mechanisms for both therapeutic and diagnostic applications.

HMAbs which recognize conformationally-defined viral epitopes and interfere with virus/target receptor interaction, and viral conformational epitopes which bind to such HMAbs, may also serve as templates for rationally designing peptide and inorganic structural mimics of the viral epitopes. Structural molecular mimics defined by these conformationally dependent anti-HCV HMAbs find use in their ability to block binding of the native virus to target receptors by binding to the target receptor themselves.

By producing human monoclonal antibodies, it is possible to directly analyze the human immune response to HCV. Importantly, by using human monoclonal antibodies, immune responses against the antibodies themselves as foreign antigens are minimal, whereas vigorous immune responses are generated against monoclonal antibodies produced from non-human sources, because they are recognized as foreign antigens. Selecting for HMAbs that recognize conformationally conserved viral epitopes affords broader and more effective therapeutic application of these reagents for ameliorating or preventing HCV infection than antibodies able to bind only linearized or denatured epitopes. All previous antibodies described as having the property of preventing HCV infection or uptake into target cells recognize a highly variable sequence of HCV E2 known as the hypervariable region. In contrast, the antibodies described above recognize conformational epitopes, the majority of which are highly conserved in HCV E2 proteins of multiple different genotypes. Thus the antibodies described herein have the advantage that they are active against a much wider range of HCV isolates than previously described neutralizing antibodies. An additional advantage is that the high conservation of the epitopes recognized by the antibodies described herein indicates that these antibodies recognize sequences with functional and/or structural significance within the HCV E2 protein. Thus peptides or small molecules isolated with these antibodies have a high probability of being targeted to functional regions within HCV E2. This is not true for other HCV antibodies described to date.

Of the detection antibodies described, CBH-4G has essentially equal reactivity to HCV E2-CD81 complexes of multiple HCV genotypes, whereas CBH-4B recognizes HCV genotypes 1a and 1b. The level of interfering antibodies present in HCV antisera has also been shown to be quite low. Therefore they provide a straightforward means of assaying the level of neutralizing antibodies present in a sample in a microtiter plate format without resorting to multiple flow cytometric analyses.

Mouse/human heteromyeloma cell lines expressing monoclonal antibody CBH-4B and CBH-4G were deposited on Jun. 18, 2002 with the American Type Culture Collection (ATCC) (10801University Blvd., Manassas, Va. 20110-

2209) and assigned ATCC numbers PTA-4466 and PTA-4468, respectively. Also included in this deposit were other mouse/human heteromyeloma cell lines expressing antibodies CBH-2 (PTA-4465), CBH-4B (4466), CBH-4D (PTA-4467), CBH-G (4468), CBH-5 (PTA-4469), CBH-7-(PTA 4470), CBH-8C (PTA-4471), CBH-11 (PTPA4472) and CBH-17 (PTA-4473), described herein below.

The overall strategy employed for the development of the subject HMAbs was as follows: (1) Individuals with evidence of exposure to HCV were identified; (2) antigen specific B-cells from their peripheral blood were expanded and activated in vitro; (3) these cells were immortalized by electrofusion with a suitable mouse-human heteromyeloma; (4) relevant human antibody secreting hybridomas were identified; and (5) the relevant hybridomas were stabilized by cloning. This strategy resulted in the identification of HMAbs which are specific to the HCV E2 protein, a number of which bound to conformation epitopes of E2 of type 1 genotypes 1a and 1b and type 2 genotypes 2a and 2b, so as to recognize the primary genotypes encountered in the United States and elsewhere with a single antibody, while others bound to fewer of the indicated genotypes, so as to be useful in identifying an HCV type or genotype.

As an example, peripheral B cells from an individual with asymptomatic HCV infection and a high serum neutralization of binding titer were used to produce and characterize a panel of human monoclonal antibodies. The initial screening made use of a genotype 1a E2 protein having an amino acid sequence with 98% homology to the same region of the HCV-1 isolate (Lanford, et al., 1993 *Virology.* 197:225–235). This step biased the screening approach used to the selection of antibodies to epitopes conserved between genotypes 1a and 1b since the donor was infected with a 1b isolate. All of the HMAbs also reacted with E2 from a heterologous HCV 1b isolate, Q1b, that was 79% homologous with the HCV 1a isolate employed in the selection of HMAbs. Denaturation of recombinant E2 completely abrogated the reactivity of 10 of 11 HCV HMAbs. Thus, the majority of the HMAbs recognized conformational epitopes.

Five HMAbs, CBH-4D, 4B, 4G, -9 and 17 were negative in the NOB assay and reacted with HCV E2-CD81 complexes. Two of these antibodies, CBH-4G and CBH-9, reacted with HCV E2 proteins of genotypes 1a, 1b, 2a, and 2b in both the GNA and CD81 capture assays. The other three antibodies, CBH-4B, 4D, and 17 exhibited restricted reactivity to E2 proteins of genotype 1a and 1b. HMAbs CBH-4B and CBH-4D have kappa and lambda lights chains, respectively, and probably recognize different epitopes. HMAb CBH-17 was the only antibody to recognize a denaturation insensitive epitope. Thus it is likely that each of the NOB negative antibodies recognize a distinct epitope.

Six of the HMAbs recognizing conformational epitopes, CBH-2, 5, 7, 8C, 8E, and 11, were positive when tested with the neutralization of binding assay using HCV 1a E2 protein. Five of these antibodies, HMAbs CBH-2, 5, 7, 8C, and CBH-8E reacted with E2 proteins of all tested genotypes. The same six antibodies failed to bind to E2. of genotypes 1a, 1b, 2a, or 2b when complexed to CD81-LEL. Thus epitopes that partially or fully overlap the CD81binding site,within HCV E2 are both conformational in nature and highly conserved. A high degree of sequence conservation in the CD81 binding site is consistent with the proposition that the interaction between HCV E2 and CD81 is biologically relevant. Two of the four NOB positive antibodies tested, HMAbs CBH-2 and CBH-5 were able to prevent the binding of intact HCV virions to CD81. The HMAbs CBH-7 and CBH-11 did not significantly inhibit binding of HCV virions to CD81, despite the antibodies having equivalent activity in the NOB assay. This may reflect the fact that HCV virions are thought to have E1–E2 complexes at their surface, and that not all of the epitopes present in E2 may be exposed in such complexes. Testing of the HMAbs with E1–E2 complexes may shed light on this issue. Alternatively, the differential results in the NOB and virion inhibition assays may reflect differences in the true affinity of the HMAbs for the E2 protein or E1–E2 complexes. In any event, a strong neutralization of binding activity in and of itself does not ensure that an antibody will bind to intact HCV virions. Thus it is probable that not all antibodies inhibiting the interaction of E2 protein with CD81-LEL in vitro will neutralize infectivity in vivo.

Five of these six NOB positive antibodies are to epitopes share among the five HCV isolates used in this study. The other antibody CBH-11 exhibited differential reactivity to two 1a isolates and probably recognizes an epitope distinct from the other antibodies. Indeed the variable reactivity of CBH-11 to different 1a isolates may have contributed to its negative result in the virion binding experiment. Both the differential reactivity of CBH-2 and CBH-7 with HCV virions and competition experiments indicate that CBH-2 and CBH-7 recognize distinct epitopes. Competition experiments also suggest that the epitopes recognized by HMAbs CBH-5 and CBH-2 are distinct. It remains possible that CBH-2 and CBH-8E recognize the same or very similar epitopes, however. Determining the total number of unique epitopes will require sequencing of the antibody genes produced by the hybridomas as well as competition studies and testing with additional HCV isolates.

These results indicate that several conformational epitopes within HCV E2 are highly conserved among divergent HCV genotypes. The antibodies that recognize these epitopes are useful as reagents to better define the structure of HCV E2. More importantly, the antibodies that inhibited binding of HCV virions to human CD81, CBH-2 and CBH-5, are prime candidates to mediate virus neutralization. The absence of a true in vitro model for virus neutralization, however, will require that the fundamental proof be obtained by the ability of selected HMAbs to prevent or modify HCV infection in appropriate animal models. If successful, broadly reactive neutralizing antibodies will likely have therapeutic utility. Analogous to the success achieved with hepatitis B immunoglobulin in liver transplantation (Dickson RC 1998 *Liver Transpl Surg* 4(5 Suppl l):S73–S78; Markowitz, et al., 1998 *Hepatology* 28:585–589), one possible application is to suppress HCV infection in liver transplant recipients with broadly reactive neutralizing human monoclonal antibodies.

While human monoclonal antibodies are provided, other antibodies from other sources may recognize the same epitopes recognized by the human antibodies described herein, and may also be employed. Generally antibodies from murine sources, mice and rats, lagomorpha and domestic animals find use. One may produce antibodies having the conserved regions of these mammalian sources using genetic engineering and replacing the constant regions of the HMAbs provided herein or may use the proteins to be described below as immunogens for immunizing the animals and then immortalizing the resulting B cells and screening as described below for immortalized cells which produce monoclonal antibodies having analogous broad range binding specificity. By screening in competitive assays with the subject HMAbs, one can determine whether the non-human antibodies bind to the same epitope.

For diagnosis, the antibodies may be used in a variety of ways, for capturing and/or identifying circulating HCV virions, E2 protein or anti-E2. The antibodies may be used for immunotherapy, prophylactic or therapeutic. The antibodies may also be used for development of vaccines for HCV.

The antibodies are of the IgG class, particularly $IgG_1$. The following are the designations for the antibodies and the HCV genotypes which the antibodies recognize. All of then HMAbs exhibited good affinity for HCV E2.proteins, with the antibodies exhibiting; maximal signals at concentrations ranging between 1 to 20µg/ml.

TABLE 1

HCV Genotypes bound by HMAbs

| Antibody | Genotypes bound |
|---|---|
| CBH-2 | 1a, 1b, 2a, 2b |
| CBH-4D | 1a, 1b |
| CBH-4B | 1a, 1b |
| CBH-4G | 1a, 1b, 2a, 2b |
| CBH-5 | 1a, 1b, 2a, 2b |
| CBH-7 | 1a, 1b, 2a, 2b |
| CBH-8C | 1a, 1b, 2a, 2b |
| CBH-8E | 1a, 1b, 2a, 2b |
| CBH-9 | 1a 1b, 2a, 2b |
| CBH-11 | -, 1b, 2a, 2b |
| CBH-17 | 1a, 1b |

The antibodies may be used in their native form or may be truncated to provide Fab or F(ab')$_2$ fragments. The genes encoding the heavy and light chains may be isolated and modified in a number of different manners. Conveniently, using RT-PCR, the cDNA may be obtained for the genes in a convenient construction for further manipulation. The nucleotide sequences of the variable regions of the heavy and light chains may be isolated and joined, either directly or through a chain of 3n nucleotides, where n is at least 1 and not more than about 60, usually not more than about 40, to provide a linker of amino acids between the two variable regions. The length of the chain can be determined empirically to provide the optimum affinity and other properties, e.g., linkage through mercapto, carboxy or amino groups, for chelation, bonding to a surface or other molecule, or the like. In addition, the genes, intact or portions thereof, including at least the variable regions, may be fused to other sequences to provide for ease of attachment to a surface, toxins for cytotoxicity, labels or tags for identification, sequences for affinity isolation, and the like.

Where labels are polypeptides, the sequence can be directly fused to a gene of one of the antibody chains. In any case, sequences may be provided which provide a site for linking a label, such as cysteines for forming thioethers with maleimide groups, polyhistidine/cysteines or polyhistidines/ aspartic acids for chelating metals, which may be bonded to a variety of molecules, polylysines for reacting with aldehydes in reductive animation, etc. Labels may include enzymes, chelating groups, ligands for binding to ligand binding proteins, e.g., biotin and streptavidin, digoxigenin and antidigoxigenin, etc., green fluorescent protein, and the like. The biotinylation sequence of E. coli biotin carboxylase carrier protein (BCCP) can be used for in vivo biotinylation of proteins expressed in E. coli or introduced into a lysate of E. coli. A sequence of six histidines or a sequence of alternating histidines and aspartic acids that are suitable for allowing binding of the antibody to a column containing immobilized divalent cations can be used. Sequences encoding high affinity epitopes may be employed, such as the FLAG epitope DYKDDDDK (SEQ ID NO: 13), the T7 tag sequence MASMTGGQMG (SEQ ID NO: 14), the S-tag sequence KETAAAKFERQHMDS (SEQ ID NO: 15), or any other sequence that confers high affinity binding to its correlative binding member or a protein reagent. Fusion proteins, besides the ones indicated above, include glutathione-S-transferase, luciferase, ligands to cell surface receptors found on hepatocytes, T-cells or other desirable cellular target, and the like. Such fusions are usually joined via a linker sequence of 3–50 amino acids that promotes the bi-functionality of the protein. These molecules can be linked to the antibodies via cleavable arms (protease sites) or other means. The antibodies may be chemically linked or fused to various toxins, such as diphtheria toxin, ricin, abrin, ribosome inactivating proteins, apoptosis signaling proteins, pore forming proteins, e.g., perforin, and the like. Alternatively, the antibodies may be linked to chelated toxic heavy metals or radioactive isotopes, particularly technetium, radioactive iodine or the like. The antibodies may be chemically linked to fluorophores or chemiluminescent molecules. Chemical coupling may involve biotinylation using the activated carboxylic acid group or biotin-C11-hydroxysuccinimide ester, which will react with cysteines; coupling through the use of CNBr activation of various beads (sepharose, agarose, magnetic, polystyrene, etc.) or surfaces to link the antibodies, and the like; any number of other methods generally involving bridging the antibody to a useful chemical moiety, usually accomplished by modifying lysine or other basic residues or through use of reagents specific for free sulfhydryl groups.

Using the genes for the heavy and light chain variable regions, particularly the hypervariable regions of the variable region may be mutated in accordance with known ways to enhance the binding affinity of the antibody or to broaden reactivity. One may use in vitro selection to identify the optimum binding antibodies using phage display methodologies, random or directed mutagenesis of sequences, or other similar methodologies. Alternatively, one may use an alanine or glycine walk of the hypervariable regions to identify essential amino acids and then vary the amino acids at those or other sites to identify improved binding of the epitope. Other techniques known in the art may be employed to provide the mutagenized antibodies.

Instead of using the hybridomas as a source of the antibodies, the genes may be isolated and introduced into an appropriate mammalian host cell, e.g. CHO, HeLa, CV1, or the like. Suitable expression plasmids are exemplified by pcDNA3.1 Zeo, pIND(SP1), pREP8 (all available from Invitrogen, Carlsbad, Calif.), and the like. The antibody genes may be expressed via viral or retroviral vectors, which may be exemplified by MLV based vectors, vaccinia virus based vectors, etc. Similarly, the antibody genes may be expressed using the pCOMB series of vectors on the surface of M13 phage, as two independent chains which may be renatured to form the intact antibody. Alternatively, the antibodies may be expressed as a single chain, including at least the variable regions. The genes may be used for gene therapy by introducing the genes into appropriate cells, such as lymphocytes, muscle cells, fibroblasts and the like, where the antibodies may be expressed and secreted, either constitutively or inductively, to provide a continuous or intermittent source of the antibodies over a predetermined period of time, based on the lifetime of the host cell. The genes in conjunction with a marker gene, e.g. antibiotic resistance, may be introduced in cell cultures of cells taken from a subject, the modified cells selected by means of the marker and the marked cells returned to the host. The DNA may be introduced into the cells using various plasmid DNA, naked DNA, DNA virus constructs, such as adenovirus, adeno associated virus, or vaccinia virus or RNA, viruses such as Vesicular stomatitis virus, sindbis virus, and semiliki forest virus to name but a few. The DNA would have a construct having a promoter for which transcription factors are present in the subject cells or can be induced or introduced and the genes under the transcriptional control of such promoter. Other regulatory sequences may also be present, such as leaders for secretion, enhancers, RNA stabilizing sequences, and the like.

For diagnostic purposes, the antibodies may be used in a wide variety of formats for detecting the E2 protein, discerning HCV genotypes, detecting virions and antibodies, see for example U.S. Pat. No. 5,695,390. The antibodies may be used individually or in combination with other of the subject group or other antibodies or with lectins which bind to the glycosyl groups present on E2, the virion envelope proteins, or other proteins with which HCV E2 complexes, e.g. HCV E1. For diagnostic purposes, a wide variety of labels may be employed, which for the most part have been mentioned previously. These include, but are not limited to, fluorophores, chemiluminescers, radioisotopes, enzymes, particles, e.g., colloidal carbon and gold, latex particles, etc., ligands for which there are high affinity receptors, and prolabels, which can be activated to provide a detectable signal.

In one embodiment, a surface is coated with a protein which will bind to HCV antigens as free or circulating proteins or as part of an intact or partially intact virion. One may use antibodies of the subject invention which bind to both type 1 and 2 HCV, or lectins, such as *Galanthus nivalis* lectin. The assay involves contacting the surface with a medium, which may contain free or virion involved protein, where the medium may be the sample or a solution of known E2 of one or more genotypes. After incubation and washing to remove non-specifically bound protein, the assay may proceed in various manners depending upon what is being assayed. Where a blood sample suspected of being seropositive is being assayed, the sample is applied to the layer of E2 protein, incubated, washed and the presence of human antibodies bound to the protein layer determined: One may use labeled anti-(human antibodies) (other than against the isotype of the subject antibodies, where the subject antibodies have been initially used). In assays for antibodies in seropositive subjects, the subject antibodies may be used as controls with the same reagent used to detect any human anti-HCV in the sera of such subjects. The specificity of the antibodies in the sample can be confirmed by using the subject antibodies which are differentially labeled from the anti-(human antibodies) and determine whether they are blocked by the antibodies in the sample.

Where the sample is assayed for HCV E2 protein, detection employs labeled subject antibodies, the selection depending upon whether one is interested in genotyping or detection of E2 protein. After washing away non-specifically bound antibody, the presence of the labeled antibodies is determined by detecting the presence of the label in accordance with known techniques. Alternatively, where the subject antibodies are bound to the surface, a labeled lectin for E2 may be employed to detect the presence of the E2 protein.

The subject antibodies can be used to measure the reactivity of other antibodies, including antibodies in sera, monoclonal antibodies, antibodies expressed as a result of genetic engineering. Desirably, intact virions are used, rather than HCV proteins, although conformationally conserved envelope proteins may also find use. For virion capture, see, for example, Kimura et al., 1998 *J. of Med. Virology* 56:25–32; Morita et al., 1996 *Hapato-Gastroenterology* 43:582–585; Sato et al., 1993 *Virology* 196:354–357; and Hijikata et al., 1993 *J. of Virology* 67:1953–1958. One protocol is to coat a solid support with a lectin, e.g., GNA, and then contact the surface with a medium, e.g., serum of a seropositive patient, comprising intact HCV virions. Additives which might destroy the virions should be avoided, e.g., detergents. After incubating the medium and washing to remove non-specifically bound components of the medium, the virions may be contacted with the antibodies of the subject invention and the antibodies of the sample. This may be performed concurrently or consecutively, where the sample is added first. An amount of the subject antibody is used which is sensitive to displacement by another antibody. Such amount may be determined empirically and one may wish to use different amounts of the subject antibody in a series of tests. By knowing the signal which is obtained in the absence and presence of the sample, one can determine the reactivity or binding affinity of the antibodies in the sample. Various techniques may be used to determine the amount of a subject antibody bound to the virions. Where the subject antibodies are labeled, e.g. biotin or digoxigenin, streptavidin or anti(digoxigenin) labeled with a fluorophore or enzyme whose substrate produces a detectable signal can serve to determine the amount of the subject antibodies.

Where the receptor (antibody or lectin) is labeled with a DNA sequence, either directly or indirectly (indirectly intends a ligand-nucleic acid sequence conjugate which can bind to empty sites of the receptor bound to the virion), by using primers homologous to the label sequence and standard conditions of the PCR, the sequence may be expanded. The DNA may then be detected in a separate hybridization reaction or by agarose gel electrophoresis. Alternatively, the Taqman approach may be used, using an internal labeled oligonucleotide probe homologous to the amplified sequence, having a light emitting label, fluorophore or luminescer, at one end and a quenching moiety at the other end. As the fragment is amplified, the 5'-3' exonuclease activity of the Taq polymerase degrades the hybridizing oligonucleotide freeing the fluorophore from the quencher, so that the fluorophore may now be detected by irradiation of the medium with light of an appropriate wavelength.

One may also use a labeled oligonucleotide probe appropriate for performing cycling probe technology. An oligonucleotide is constructed of about 15–20 deoxynucleotides homologous to the label and having a TM$\leq$45° C., a sequence of about 5 or more ribonucleotides homologous to the internal sequence, followed by about 15–20 deoxynucleotides homologous to the label and having a TM$\leq$45° C. The intact oligonucleotide will have a TM>60° C. The oligonucleotide is further modified as described above with a light emitting label and a quencher label. After adding an excess of the oligonucleotide construct to the bound label and allowing it to hybridize to the bound label at a temperature of about 55° C., RNase H, active at 55° C. is added to degrade the ribonucleotides. Upon denaturation the light emitting label will be released and free of the quencher and upon irradiation or activation its light emission determined.

Alternatively, transcription mediated amplification (TMA) may be employed. In this case, the bound oligonucleotide label contains a promoter recognized by T7 polymerase or other convenient polymerase. Addition of T7 or other appropriate polymerase and rNTPs under, appropriate conditions results in the transcription of the bound oligonucleotide to oligoribonucleotides, which can then be detected by any convenient means, e.g., electrophoresis.

Labeled subject antibodies may be used in assaying for the presence of HCV from biopsy material. Labeled antibody may be incubated with immobilized biopsy material, such as a liver slice, with a solution of one or more of the subject labeled antibodies. After washing away non-specifically bound antibodies, the presence of the antibodies bound to the cells of the biopsied tissue may be detected in accordance with the nature of the label.

Conformationally conserved E2 genotype proteins 1a, 1b, 2a and 2b, the latter two being novel expression compositions are provided as proteins expressed from vaccinia virus constructs. Their preparation is described in the experimental section. The proteins are obtained free of amino acids of E1 proteins, although they can be prepared from genes encoding both E1 and E2, where the resulting fusion protein is processed to provide the two proteins which are no longer covalently joined, but may exist as a complex. The proteins may be isolated from a lysate or from the medium where the construct allows for secretion. The protein may be readily purified using affinity chromatography, HPLC or non-denaturing gel electrophoresis. The proteins may be obtained in purities exceeding 95 wt. %, usually at least 99 wt. %. The proteins may be used in assays for genotyping sera from HCV infected patients, in screening monoclonal antibodies for affinity and specificity, for evaluating drugs where the proteins are the target of the drugs, for immunizing mammalian hosts for the production of antisera and monoclonal antibodies, and the like. Their use in diagnostic assays has already been discussed.

Figure 9:
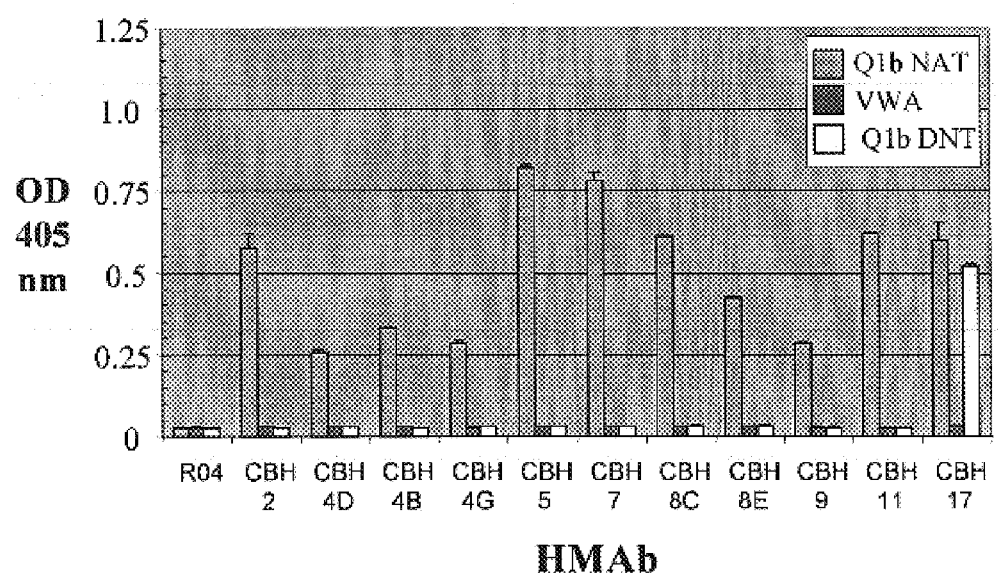
FIG. 9 is a bar graph showing the reactivity of HCV HMAbs with native (NAT) and denatured (DNT) HCV 1$b$ E2 protein. Cytoplasmic extract derived from $6 \times 10^5$ HeLa cells infected with vaccinia virus Q1b and VWA or VWA alone were either left untreated (blue bars) or denatured by incubation with 0.5% SDS and 5 mM dithiothreitol for 15 minutes at 56° C. (yellow bars). After treatment, proteins were diluted 1:5 in BLOTTO and captured onto wells coated with 500 ng of GNA lectin. Wells were washed and blocked and bound protein was incubated with the indicated concentration of HCV HMAbs and control HMAb (R04). Bound antibody was detected with anti-human IgG alkaline phosphatase conjugate and PNPP. Color development was allowed to proceed for 45 minutes. Values for native and denatured HCV 1b are the mean signal obtained from replicate wells. Signals from single wells of native and denatured proteins derived from VWA infected HeLa cells were indistinguishable and also averaged (red bars). Error bars indicate one standard deviation from the mean.

The antibodies may used to identify the structural epitopes on E2 proteins that they bind. Two basic approaches may be employed using the monoclonal antibodies for identifying conformational epitopes. In the first, natural variants or mutation analysis of HCV isolates may be used to identify regions, and ultimately individual amino acids that are involved in the epitopes recognized by the monoclonal antibodies (Schwartz, et, al., 1999 *J Mol Biol.* 287:983–999). The antibodies are screened against a number of different HCV E2 isolates, identifying isolates that are selectively non reactive with individual antibodies. For example, HMAb CBH-11 reactivity with HCV E2 protein Q1a is reduced compared to its reactivity with HCV E2 Q2a (FIG. 9). "Chimeric" E2 envelope proteins are then be constructed in which portions of the chimera are derived from E2 proteins from one HCV genotype and other portions are derived from E2 proteins of another HCV genotype. These chimeric E2 proteins are constructed by PCR ampilfying overlapping fragments, and/or by using restriction sites common to both E2 proteins. An alternative method is DNA shuffling as pioneered by the Biotechnology company Maxy-Gen. By surveying the observed binding reactivities of different chimeric E2 proteins with different monoclonal antibodies, amino acid regions in the E2 proteins critical in forming conformational epitopes are identified. Once the critical regions are identified, individual amino acids that differ between the different genotypes are mutated to compose a reactive E2 sequence. Mutants that restore full reactivity identify amino acids that are involved in forming the epitope.

A second basic approach to defining a conformational epitope is to synthesize a series of overlapping peptides 10–15 residues in length that encode the desired sequence of HCV E2. These peptides are then screened against the antibodies using high concentrations of antibody (often 100 ug/ml or higher). Individual regions that comprise the full conformational epitope often retain residual binding activity with the antibody that can be detected. Once these regions are identified, they can be confirmed using mutational studies involving the 10–15 residues of the peptide, either in the context of the peptide or by substituting into a conformationally intact HCV E2 protein. A variation of this methodology is described in (Reineke et al., Nature Biotechnology, Vol 17, 1999 271–275).

The subject antibodies also may be used for screening for mimotopes. Mimotopes may be prepared using phage display and the peptides screened with the subject antibodies (Livnah et al., 1996 *Science* 273:464–471; Prezzi, et al., 1996 *J. Immunol.* 156:4504–4513). Antibodies that recognize conformationally conserved HCV epitopes may be used as templates for the rational design of peptide or non-peptide structural mimics of the conformational epitope or mimotopes.

The generation of mimotopes is biologically significant. By mimicking the structure of the conformationally defined viral epitope, the mimotope can interfere with the ability of the virus to bind its target receptor by binding to the receptor itself. For example, analysis of a solved crystal structure defining the interface between a monoclonal antibody and tumor necrosis factor (TNF) enabled the rational design of a non-peptide mimetic capable of antagonizing the biological function of TNF by binding to the TNF receptor (Takasaki , et al., 1997 *Nat Biotech.* 15:1266–1270). Computational techniques that may be employed to rationally deduce protein folding from a primary amino acid sequence for use in designing a peptide structural mimetic are reviewed in Teichmann, et al., 1999 *Curr Opin Struct Biol.* 9:390–399. The practical application of computer programs for use in structurally modeling conformationally conserved epitopes is described by Schwartz, et al., 1999 *J Mol Biol.* 287:983–999. An alternative method for rationally creating a peptide structural mimic of an antibody epitope involves systematic permutations of synthetic peptides designed to be a linear representation of a discontinuous antibody binding site (Reineke, et al., 1999 *Nat Biotech.* 17:271–275).

Peptides, or other small molecules having specific affinity for a monoclonal antibody and competitive with an epitope of a conformationally intact E2 protein, by itself or complexed with E1, may be used as vaccines, in diagnostic assays, for immunization for the production of antibodies to a specific HCV epitope, in competitive assays for defining genotype, and the like. See, for example, Puntoriero et al., 1998 *EMBO J* 17:3521–3533; Meola et al., 1995, *J. Immunol.* 154:3162–3172; Tafi et al., 1997 *Biol. Chem.* 378:495–502.

Another approach to effectively create structural mimetics of conformationally conserved HCV epitopes is to produce anti-idiotypic antibodies to the conformationally dependent anti-HCV HMAbs. Anti-idiotypic antibodies may effectively block the binding of native virus with its target receptor (Chanh, et al., 1987 *Proc Natl Acad Sci.* 84:3891–3895; Kopecky, et al., 1999 *Intervirol.* 42:9–16 and Xue, et al., 1993 *J Gen Virol.* 74:73–79). Anti-idiotypic antibodies recognizing the conformational binding sites of any one of the anti-HCV HMAbs CBH-2, 5, 4B, 4D, 4G, 7, 8C, 8E, 9, or 11 could prevent viral infectivity by interfering with E2 binding to a target cellular protein, or even by interfering with virion attachment to the target cell.

The subject antibodies find use for prophylactic therapy or for treating HCV infection, by reducing viral load, by inhibiting binding of the virus to it's target proteins, by inhibiting virus mediated fusion with a target cell and by interfering with conformational changes in the viral envelope proteins necessary for cell infectivity. The composition used can be a monoclonal antibody directed to a single conformational epitope, or a mixture of complementary monoclonal antibodies that recognize distinct conformational epitopes on one or more viral envelope proteins, thereby simultaneously interfering with multiple mechanisms in the infectious process.

For reducing viral load of a body component, particularly a body component of a patient infected with HCV, patient blood is passed through a device comprising the antibodies bound to a surface for capturing the HCV. See, for example, U.S. Pat. Nos. 5,698,390 and 4,692,411. Various other devices found in the literature can be used with the subject antibodies to achieve a similar result. A body component can be a biological fluid, a tissue, an organ, such as the liver, and the like.

The antibodies also may be used for passive immunization therapies or other in vivo therapies. See, for example, Piazzi, et al., 1997 *Arch Intern Med.* 157:1537–1544; Farci, et al., 1996 *Proc Natl Acad Sci.* 93:15394–15399; al-Hemsi, et al., 1996 *Clin Transplant.* 10:668–675; Krawczynski, et al., 1996 *J Infect Dis* 173:822–828). For such therapeutic use, the antibodies may be formulated in any convenient way for injection or intravenous administration. Various media may be used such as phosphate buffered saline, saline or the like. The amount of the antibodies may be varied depending on the level of infection, the affinity of the antibodies, the manner of administration, the frequency of administration, the response of the patient, the use of other therapeutics, and the like. Generally the amount of antibody administered will be in the range of about 0.1 to 5 mg/kg. See, for example, Andrus et al., 1998 *J. Infect. Dis.* 177:889–97 and Kreil et al., 1998 *J Virology* 72:3076–3081.

The chimpanzee is an accepted animal model for screening HCV vaccines and therapeutics. See, for example, Farci, et al., 1996 *Proc Natl Acad Sci.* 93:15394–15399; Farci, et al., 1994 *Proc Natl Acad Sci* 91:7792–7796; Farci, et al, 1992 *Science* 258:135–140; Krawczynski, et al., 1996 *J Infect Dis* 173:822–828; Bassett, et al., *J Virology* 72:2589–2599. The effectiveness of the antibodies can be determined by monitoring for the presence and titer of HCV RNA using quantitative PCR methods. A successful reduction of viral load, or prevention of infection in a test animal or subject is reflected as a reduction or elimination of HCV RNA in serum. Enzymatic tests such as measurement of alanine aminotransferase and/or use of sequential punch needle liver biopsies also is used to test effectiveness, where improvement in the rating of either would indicate a reduction in viral-induced liver damage.

The following examples are offered by way of illustration and not by way of limitation.

EXAMPLES

Example 1

Production of HCV E2 Proteins From Multiple Genotypes in Vaccinia Virus

To analyze the reactivity of HCV sera and test the breadth of HCV-HMAbs reactivity, the complete coding sequence of HCV were cloned from isolates of HCV genotypes 1a, 1b, 2a, and 2b, were PCR amplified from HCV positive sera and expressed with vaccina virus using the pVCTE (Ward, et al., 1995 *Proc Natl Acad Sci USA.* 92:6773–6777) transfer vector (constructs Q1a, Q1b, Q2a, and Q2b for HCV genotypes 1a, 1b, 2a, and 2b, respectively). Genotype selection was based on its divergence and frequency among HCV infected individuals in the United States (Mahaney, et al., 1994 *Hepatology* 20:1405–1411). Oligonucleotide primers were designed to amplify fragments that expressed the final 39 amino acids of E1, all of E2/p7, and the N-terminal 98 amino acids of NS2. See Table 2. (SEQ ID NOS: 18–27)

Accordingly, aliquots of plasma from individuals PCR positive for HCV RNA were obtained and genotyped using the InnoLipa HCV genotyping assay performed according to manufacturers instructions (Innogenetics, Ghent, Belgium). RNA was prepared from 125 μl of plasma from individuals infected with HCV genotypes 1a, 1b, 2a, and 2b using the Purescript RNA kit, according to manufacturer's instructions (Gentra Systems, Minneapolis Minn.). RNA pellets were re-suspended in 25 μl of RNAse free H$_2$0 and 10 μl was subjected to reverse transcriptase PCR. Reverse transcription reactions were performed using MMLV reverse transcriptase employing the reverse HCV specific primer HCV E2-R1 5'-CGC GCA CrA AGT AsG GyA CT-3' (SEQ ID NO; 16). Reverse transcription was for 60 minutes at 40° C. Reverse transcribed cDNA was denatured by a 5 minute incubation at 98° C. followed by cooling to 4° C. and the addition of PCR mix containing 0.15 mM dNTPs, 3μl 10×PCR buffer, 3 units of Amplitaq polymerase, and the forward primer HCV E2-F1 5'-CGC ATG GCi TGG GAy ATG ATG -3' (SEQ ID NO: 17). Amplification was for 30 cycles of 94° C. for 1 minute, 55° C. for 3 minutes, and 72° C. for 3 minutes. Between 2 to 8 μl of amplified product was then subjected to a second round of PCR amplification with using the forward primer appropriate for cloning each genotype and an internal reverse primer INT-Reverse (Table 2, SEQ ID NOS: 18–27) or the reverse primer appropriate for each genotype and INT-Forward. PCR amplifications were for 30 cycles of 94° C. for 1 minute, 60° C. for 2.5 minutes, and 72° C. for 2 minutes. Appropriately sized bands (~820 nucleotides for the genotype specific forward primer and INT-Reverse and ~1080 nucleotides for INT forward and the genotype specific reverse primer) and

TABLE 2

Primers[1] employed in cloning HCV E2 protein

| Gtyp | Foward Primer | SEQ ID NO. |
|---|---|---|
| 1a | CG AAG CTT <u>CAT ATG</u> ATC GCT GGT GCT CAC TGG<br>Nde I | 18 |
| 1b | CG CAT ATG <u>GAG CTC</u> GCG GGG GCC CAC TGG GGA GT<br>Sac I | 20 |
| 2a | C GCT CGA <u>GCC ATG G</u>TT GGC GGG GCT CAT TGG GGC<br>Nco I | 22 |
| 2b | C GCT CGA <u>GCC ATG G</u>TT TTC GGC GGC CAT TGG GTG<br>Nco I | 24 |

TABLE 2-continued

Primers[1] employed in cloning HCV E2 protein

| Gtyp | Reverse Primer | SEQ ID NO. |
|---|---|---|
| INT | TG GTT CGG BTG YWC ITG GAT GAA | 26 |
| 1a | GC GGA TCC <u>CTG CAG</u> CTA CAA ACT GGC TTG AAG AAT CCA<br>       Pst I | 19 |
| 1b | GC TCT AGA <u>CTG CAG</u> CTA TAT GCC AGC CTG GAG CAC CAT<br>       Pst I | 21 |
| 2a | TC GAA TTC <u>GGA TCC</u> TAC AAA GCA CCT TTT AGG AGA TAA GC<br>       BamH 1 | 23 |
| 2b | TC GAA TTC <u>GGA TCC</u> TAC AGA GAC GCT TTA AGG AGG TAG GC<br>       BamH I | 25 |
| INT | TAA TGC CAi ARC CKR TAi GGG TAG TC | 27 |

[1] Inner nested primers employed in cloning of vaccinia virus E2 constructs. The restriction sites employed in the cloning are underlined. The primers contained additional restriction sites in their 5' ends. The primers contain other restriction sites. Gtyp = HCV genotype. The primers INT-F and INT-R contain degenerate nucleotides and were used for all genotypes. PCR amplification conditions are described in Example 1.

were excised from ethidium-bromide stained agarose gels and purified using a commercially available resin (Qiagen, Valencia, Calif.). Approximately 50 ng of each band were combined and re-amplified with the forward and reverse primers appropriate for each genotype (Table 2). PCR amplifications were for 30 cycles of 94° C. for 1 minute, 55° C. for 2.5 minutes, and 72° C. for 2 minutes. The amplified products were then excised from ethidium bromide stained agarose gels, purified, and digested with the appropriate restriction enzymes. This 3 step amplification procedure resulted in a much higher yield of full-length insert than standard two-step procedures. The digested DNAs were then ligated into a similarly digested pVOTE 1 or pVOTE 2 vector (Ward, et al., 1995 *Proc Natl Acad Sci USA* 92:6773–6777). The ligated plasmids were transfected into competent *E. coli* and insert-containing clones were identified and propagated using standard methods (Sambrook J, Fritsch E and Maniatis T. *Molecular Cloning: A Laboratory Manual. Cold Spring Harbor Press,* Cold Spring Harbor, N.Y., 1989). The clones obtained were designated Q1a, Q1b, Q2a, and Q2b for constructs expressing full length E2 and p7 of. HCV. genotypes 1a, 1b, 2a and 2b, respectively. Expression of intact E2 protein by vaccinia virus constructs Q1a and Q2b was verified in a transient expression assay. CV-1 cells were infected with 5 plaque forming units (pfu) of wild type vaccinia virus strain VWA (Ward et al. supra) and then transfected with pVOTE plasmid using Transfectam (Promega, Madison, Wis.), according to the manufacturer's instructions. Cells were cultured in media supplemented with 1 mM Isopropyl-β-D-thiogalactopyranoside (IPTG) to induce expression of HCV proteins (Ward, et al. supra). Forty eight hours after transfection the cells were harvested by washing cultured cells with PBS and resuspending the cells in lysis buffer (150 mM NaCl, 20 mM Tris pH 7.5, 0.5% deoxycholate, 1.0% Nonidet-P40, 1 mM EDTA) to which the protease inhibitors Pefabloc (Boehringer Mannheim, Indianapolis, Ind.), Aprotinin, Leupeptin, and Pepstatin were added to final concentrations of 0.5 mg/ml, 2 µg/ml, 2 µg/ml and 1 µg/ml, respectively. One hundred microliters of lysis buffer was added for every 3×10$^6$ cells harvested. Nuclei were then pelleted by centifugation at 18,000×g at 4° C. for 10 minutes and the supernatant was either used directly or stored at 4° C. for not more than two days prior to use.

For Western blot analysis, 10 µl of lysis buffer extract was combined with 10 µl of 2×SDS sample buffer (20% glycerol, 10% β-mercaptoethanol, 4.8% SDS, 0.125 mM Tris pH 6.8, heated to 95° C. for 5 minutes, and fractionated by sodium dodecyl sulfate-polyacrylamide gel electrophoresis (SDS-PAGE) (Laemmli, et al., 1970 *Nature* 227:680–685) employing 12% polyacrylamide gels. The fractionated proteins were then electrotransferred to nitrocellulose and incubated overnight with murine monoclonal antibody (mMab) 2C8 that recognizes Western blotted HCV E2 (available from Dr. H. Greenberg, Stanford University). mMAb 2C8 was diluted 1:500 in BLOTTO (2.5% non fat dry milk, 2.5% normal goat serum, 0.1% Tween-20 (Sigma, St. Louis, Mo.), 0.02% sodium azide in TBS: 150 mM NaCl, 20 mM Tris, pH 7.5). Purified HCV or control antibodies or HMAb-containing culture media diluted to an IgG concentration of 5 µl/ml in BLOTTO. The blots were washed 3 times with TBS, and bound antibody was detected with the ECL Western blot kit, according to manufacture's instructions (Amersham, Arlington Heights, Ill.).

The constructs Q1a and Q2b produced an approximately 70 kdal protein that was immnoreactive with mMAb 2C8 (FIG. 1). As expected with the pVOTE system (Ward, et. al., 1995 *Proc Natl Acad Sci USA* 92 6773–6777,) the expression of the HCV E2 proteins was highly dependent on the presence of the inducer IPTG. Expressed protein was also detected from all 4 constructs by IFA with a panel of 10 genotyped HCV sera (data not shown). None of the constructs were reactive with HCV-negative sera nor did any of the HCV antisera react with cells infected with wild type vaccinia virus.

The genotypes of the cloned E2 proteins were confirmed by DNA sequencing of either a 160 bp internal fragment (nts. 2009 to 2168 of HCV-1) from the center of HCV E2 from each of the four clones. See FIG. 2 (SEQ ID NOS: 9–12), or the entire insert (construct Q1b) employing dye terminator methodologies and an automated DNA sequencer (Applied Biosystems, Foster City Calif.). The inserts were highly homologous to the appropriate sequences of HCV E2 available in various databases with no frame shift or termination mutations. See FIG. 3 (SEQ ID NOS: 1–8). Thus, this is good evidence that HCV E2 of all 4 genotypes was accurately expressed by the pVOTE constructs. Plasmids that produced intact HCV were then used to generate recombinanat vaccinia virus by homologous recombination into the hemaglutinin locus of the vaccinia virus strain VWA (Ward, et al., supra as described Moss and Earl.In F. Ausubel and R Brent and R Kingston (ed.), *Current Protocols in*

*Molecular Biology*, Vol. 2, John Wiley & Sons, New York, N.Y., 1994). Recombinant vaccinia viruses were identified via infection of BSC-1 cells followed by selection for guanine phosphoribosyl transferase containing virus with media containing mycophenolic acid, xanthine, and hypoxanthine, using standard methods (Moss, et al., supra). Purified viral stock was obtained for each recombinant virus and titers measured using BSC-1 cells ranged between 5–10×10$^8$ pfu/ml.

Example 2

Antibody Screening of Potential HCV Positive B-cell Donors

Since HCV cannot be reliably propagated in vitro, it is necessary to use recombinant envelope proteins expressed in eukaryotic cells to identify-individuals with strong antibody titers to HCV proteins. In such screening it is necessary to use methods that preserve the native structure, of the envelope proteins thus allowing the detection of antibodies to conformational epitopes. In the identification of sera for the generation of HCV HMAbs an indirect immunofluorescent assay (IFA), was employed. This assay uses acetone-fixed cells and is analogous to methods used in the production of neutralizing HMAbs to conformational epitopes on human T-lymphotropic virus envelope protein (Hadlock et al., 1997 *J. Virology* 71:5828–5840). For HCV, acetone-fixed cells expressing HCV E2 envelope proteins were used. At various points the E2 proteins were expressed using recombinant baculovirus in SF9 cells, recombinant vaccinia virus in HeLa cells, as described above, or in chinese hamster ovary (CHO) cells using a commercially available vector (pDisplay, In Vitrogen, Carlsbad, Calif.). Since insect derived cells may not express viral envelope proteins in a truly native conformation (Rosa et al Supra, Arp et al, 1996 *J Virology*, 70:7349–7359.) the use of vaccinia virus or mammalian cell expression systems is preferred. The fluorescence observed with a given serum was scored visually via fluorescence microscopy and in some cases increasing dilutions of the sera were evaluated to obtain and end point dilution titer of the potential donor sera.

To confirm results obtained with immunofluoresence we also went on to develop a microtiter plate assay for evaluating the reactivity of sera to HCV E2. Monolayers of HeLa cells were grown to 80% confluence and infected with 5 pfu/cell of VWA and 5 pfu/cell of recombinant vaccinia virus or 5 pfu of VWA only. HCV recombinant viruses were mixed with wild type vaccinia with an intact hemaglutinin gene to minimize the vaccinia virus induced cytopathic effect observed with hemaglutinin minus virus (Seki et al. 1990, *Virology* 175:372–384). Twenty-four hours after infection cells were harvested. Extracts were prepared by washing the cells with PBS and then resuspending 30×10$^6$ cells in I ml of lysis buffer (150 mM NaC1, 20 mM Tris pH 7.5, 0.5% deoxycholate, 1.0% Nonidet-P40, 1 mM EDTA, 0.5 mg/ml Pefabloc (Boehringer Mannheim, Indianapolis, Ind.), 2 µg/ml Aprotinin, 2 µg/ml Leupeptin, and 1 µg/ml Pepstatin). Nuclei were pelleted by centrifugation at 18,000×g at 4° C. for 10 minutes. Extracts were stored at 4° C. and used for ELISA within 24 hours of preparation. Microtiter plats (Maxisorp, Nalge Nunc International, R6Rochester, N.Y.) were prepared by coating individual wells with 500 ng of purified *Galainthus nivalis*, lectin (obtained from SIGMA, St. Louis, Mo.) in 100 µl of PBS for 1 hour at 37° C. Wells were then washed with TBS (150 mM NAC1, 20 mM Tris-HCL, pH 7.5), and blocked by incubation for 1 hour at room temperature with 150 µl BLOTTO (TBS plus 0.1% Tween-20, 2.5% normal goat sera, 2.5% non fat dry milk). Plates were washed two times with TBS followed by the addition of 20 µl of extract from vaccinia virus infected HeLa cells 1:5 with BLOTTO. After incubation for 1.5 hours at room temperature, plates were washed three times with TBS followed by addition of HCV sera at various dilutions in 95 µl of BLOTTO supplemented with 5 µl of soluble extract from HeLa cells infected with vaccinia virus VWA. The inclusion of the soluble extract served to suppress reactivity to vaccinia virus proteins that might also be captured by GNA lectin. Plates were incubated for 1.5 hours, wells were washed three times with TBS and 100 µl of anti-human alkaline-phosphatase conjugate (Promega, Madison, Wis.) diluted 1/5000 in BLOTTO was added. After incubation for 1 hour at RT, the plates were then washed four times with TBS followed by incubation with a 1 mg/ml solution of p-nitrophenyl phosphate (PNPP). Substrate development was allowed to proceed for 30 to 45 minutes, then the absorbence of the wells at 405 nm was determined using a multiwell plate reader (Du Pont Co, Wilmington, Del.).

Figure 4:
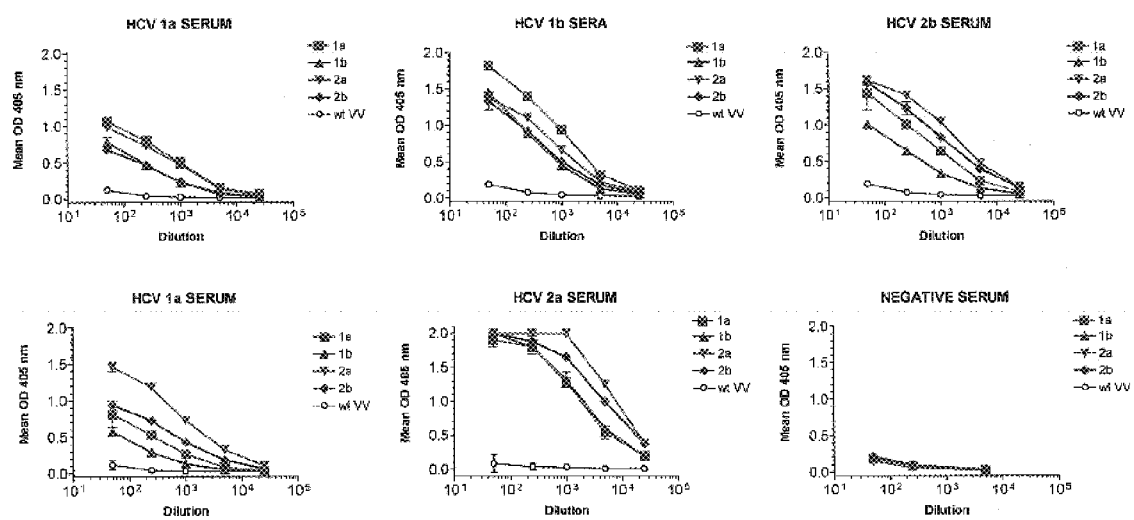

Typical results are presented in FIG. 4. In this experiment five genotyped HCV sera and one serum from an HCV negative blood donor were titrated against HCV E2 proteins of genotypes 1a, 1b, 2a, and 2b, as well as proteins captured from extracts infected with non-recombinant vaccinia virus VWA. Minimal reactivity to the HCV E2 was observed with a serum from an uninfected individual (Graph labeled Negative Serum). Additionally all five sera from HCV infected individuals exhibited little or no reactivity to proteins captured from extracts infected with wild type vaccinia virus (thin black lines, all graphs). It can be appreciated that a wide variation in seroreactivity to HCV E2 proteins was obtained with the five sera tested, with the HCV 2a individual exhibiting the highest overall reactivity.

Figure 5:
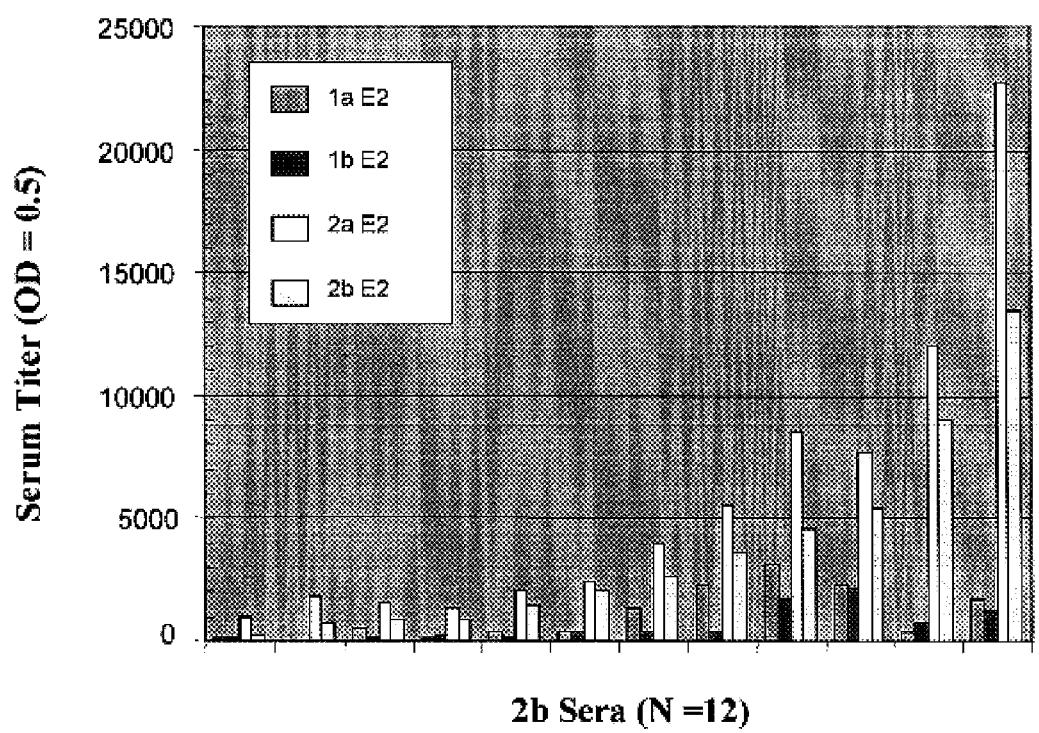

The results obtained with 12 sera from individuals infected with HCV genotype 2b are presented in FIG. 5. In this graph the dilution of sera that resulted in a specific OD of 0.5 for all four of the HCV. E2. proteins is compared (Specific OD is the OD obtained from wells coated with extract of HCV E2 construct—OD of wells coated with extract of non-recombinant vaccinia virus). For all 12 sera, reactivity to HCV 2b or 2a E2 protein was significantly greater than that obtained with HCV 1a or 1b E2 protein. This indicates the superiority of HCV genotype 2 E2 proteins for the detection of antibodies recognizing the HCV envelope in individuals infected with HCV genotype 2a or 2b. Also, the individuals presented on the right side of the graph would be more promising donors for the isolation of HCV HMAbs specific for epitopes present in genotype 2a or 2b E2 proteins.

The donor employed to generate the HCV HMAbs was identified as HCV seropositive with the first generation HCV screening assay during a course of autologous donation. Alanine aminotransferase (ALT) testing of the donated units resulted in 6 out of 7 of the donations being within the normal range (<45 IU). One donation had an ALT value of 49, which is just over the normal cutoff. Otherwise the donor exhibited no outward symptoms of hepatitis. This individual was later confirmed to be HCV positive by PCR using the Roche amplicor HCV assay (Roche Diagnostics, Branchburg, N.J.) and was determined to be infected with HCV of the 1b genotype by the InnoLipa probe assay (Innogenetics, Ghent, Belgium). This individual was found to have a high titer of antibodies capable of recognizing HCV E2 using IFA. Testing with the neutralization of binding assay (see below) also indicated this donor had a high titer of potentially neutralizing antibodies. Peripheral blood B-cells were isolated from this individual and successfully used to generate HCV antibody secreting human hybridomas (described below).

Example 3

Production of Antigen-specific Human Monoclonal Antibodies

Peripheral B-cells were purified from donor T-cells by T-cell resetting as described (Foung et al., 1984 *J. Immunol. Methods* 134:35–42) which disclosure is incorporated by reference. Individual cultures of 1×10⁴ B-cells were EBV-activated in microtiter plates. HCV specific antibodies were detected with an immunofluorescence assay (IFA). Cells infected with recombinant vaccinia virus expressing HCV E2 proteins, recombinant baculovirus expressing HCV E2,and/or mammalian cell lines that have been engineered to express HCV E2 from their DNA were fixed onto HTC supercured 24-spot slides. The cells were fixed with 100% acetone for 10 minutes at room temperature. Fixed cells were incubated with undiluted culture media from EBV activated B cells or hybridomas for 30 minutes at 37° C. and washed for 5 minutes with phosphate buffered saline (PBS), pH 7.4. Slides were then incubated for 30 minutes at 37° C. with 0.001% solution of Evan's blue counterstain and fluorescein isothiocyanate (FITC) conjugated goat-anti-human IgG (Zymed, South San Francisco, Calif.). Bound antibody was revealed by fluorescence microscopy.

Out of 540 cultures, 99 wells showing significant immunofluorescence to HCV E2 were identified (yield~18%) and 30 of the EBV-activated cultures with different immmunofluorescence patterns were selected for electrofusion to mouse-human heteromyelomas as described (Foung et al., 1990 *J. Immunol. Methods* 134:35–42; Zimmerman, et al., 1990 *J. Immunol. Methods* 134:43–50; and Perkins, et al., 1991 *Hum. Antibod. Hybridomas* 2:155–159). Out of 12 fusions (some fusions contained more than one positive EBV activated culture), 182 out of 456 initial hybridoma cultures exhibited reactivity with HCV E2 by IFA (yield 40% overall). Six additional fusions were performed on two of the original EBV-activated cultures that showed reactivity to HCV-E2 by Western blot. Hybridomas secreting HCV E2 antibodies reactive by Western blot (in addition to being IFA reactive) were isolated from 2 of the fusions. Overall, 30 human hybridomas were frozen. Limiting dilution clones were isolated from 12 parent hybridomas and HCV-HMAbs from 11 of the hybridomas were produced in bulk for subsequent studies. Eight of the HCV HMAbs were $IgG_1$ with kappa light chains and two were $IgG_1$ with lambda light chains. HMAb CBH-9 was IgG1 but it is not known whether it uses a lambda or kappa light chain. PCR and DNA sequence analysis of 10 of the HMAbs (the lone exception was HMAb CBH-9) confirmed that all of the HMAbs expressed distinct heavy and light chains. The fusion partners, IgG subtypes, and results obtained in IFA with the hybridomas are described in Table 3.

Example 4

HCV E2 ELISA

Figure 6:
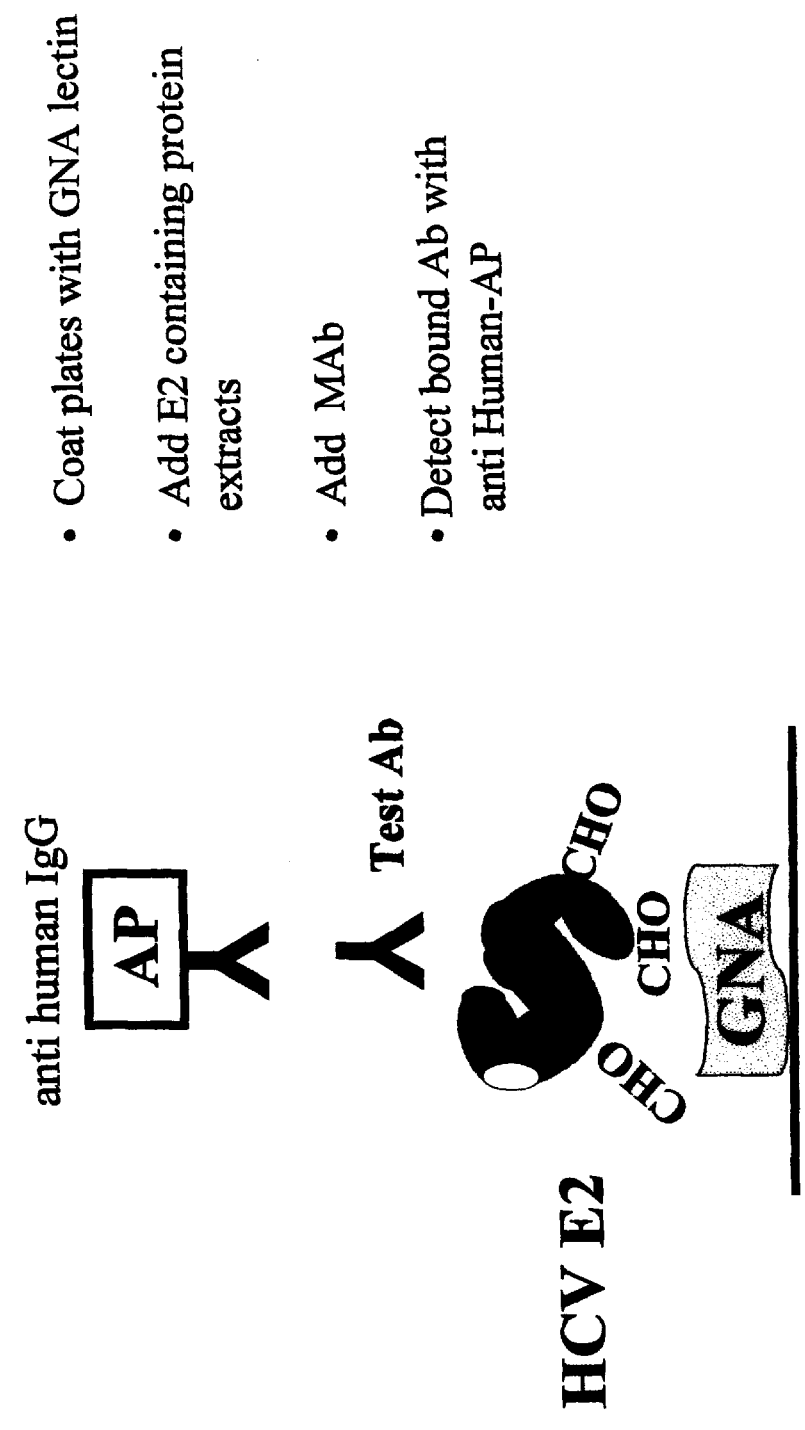

Previous: studies indicated that the HCV E2 protein is highly glycosylated and can be bound by any one of several lectins including *Galanthus nivalis* (GNA), *Tiriticum vulgaris* (WGA), and *Ricinus communis* (Ralston, et al., 1993, supra; da Silva Cardosa, 1998, supra; and Sato et al., 1993 *Virology* 196:354–357). Therefore the utility of the two lectins GNA and WGA as reagents was evaluated for capturing HCV E2 protein onto a microtiter plate. A schematic of this assay is depicted in FIG. 6. 25 Monolayers of HeLa cells were grown to 80% confluence and infected with 5 pfu/cell of VWA and 5 pfu/cell of recombinant vaccinia virus or 5 pfu of VWA only. HCV recombinant viruses were mixed with wild type vaccinia with an intact hemaglutinin gene to minimize the vaccinia virus induced cytopathic effect observed with hemaglutinin minus virus (Seki et al. 1990, *Virology* 175:372–384). Twenty-four hours after infection cells were harvested. Extracts were prepared by washing the cells with PBS and then resuspending 30×10⁶ cells in 1 ml of lysis buffer

TABLE 3

Characteristics and IFA reactivity of HCV HMAbs

| Antibody[a] | Hetero Myeloma | Subtype Heavy | Subtype Light | Immunofluorescence 1a | 1b | 2a | 2b |
|---|---|---|---|---|---|---|---|
| CBH 2 | $K_6H_6/B5$ | IgG1 | Kappa | ++ | ++ | ++ | ++ |
| CBH 4D | $K_6H_6/B5$ | IgG1 | Lambda | + | + | – | – |
| CBH 4B | $K_6H_6/B5$ | IgG1 | Kappa | ++ | ++ | +/– | – |
| CBH 4G | $K_6H_6/B5$ | IgG1 | Kappa | + | + | +/– | +/– |
| CBH 5 | H73C11 | IgG1 | Kappa | ++ | ++ | ++ | ++ |
| CBH 7 | $K_6H_6/B5$ | IgG1 | Kappa | ++ | ++ | ++ | ++ |
| CBH 8C | $K_6H_6/B5$ | IgG1 | Kappa | ++ | ++ | ++ | ++ |
| CBH 8E | $K_6H_6/B5$ | IgG1 | Kappa | ++ | ++ | ++ | ++ |
| CBH 9 | H73C11 | IgG1 | Unknown | + | + | +/– | +/– |
| CBH 11 | $K_6H_6/B5$ | IgG1 | Kappa | + | ++ | ++ | ++ |
| CBH 17 | $K_6H_6/B5$ | IgG1 | Lambda | + | ++ | – | – |
| R04 | | IgG1 | Lambda | – | – | – | – |

[a]Reactivity by IFA of HCV HMAbs with HeLa cells infected with recombinant vaccinia virus expressing HCV E2 of the indicated genotype. Reactivity was scored ++ strongly positive; + positive; +/– weakly positive; – negative. The heavy and light chain subtypes of the antibodies are provided. R04 is an isotype matched control antibody. Antibodies were tested at 10 µg/ml.

(150 mM NaCl, 20 mM Tris pH 7.5, 0.5% deoxycholate, 1.0% Nonidet-P40, 1 mM EDTA, 0.5 mg/ml Pefabloc (Boehringer Mannheim, Indianapolis, Ind.), 2 µg/ml Aprotinin, 2 µg/ml Leupeptin, and 1 µg/ml Pepstatin). Nuclei were pelleted by centrifugation at 18,000×g at 4° C. for 10 minutes. Extracts were stored at 4° C. and used for ELISA within 24 hours of preparation.

Microtiter plates (Maxisorp, Nalge Nunc International, Rochester, N.Y.) were prepared by coating individual wells with 500 ng of purified lectin in 100 µl of PBS for 1 hour at 37° C. Wells were then washed with TBS (150 mM NAC1, 20 mM Tris-HCL, pH 7.5), and blocked by incubation for 1 hour at room temperature with 150 µl BLOTTO (TBS plus 0.1% Tween-20, 2.5% normal goat sera, 2.5% non fat dry milk). Plates were washed two times with TBS followed by the addition of 20 µl of extract from vaccinia virus infected HeLa cells 1:5 with BLOTTO. After incubation for 1.5 hours at room temperature, plates were washed three times with TBS followed by addition of unlabeled antibodies at various concentrations in 100 µl of BLOTTO. Plates were incubated for 1.5 hours, wells were washed three times with TBS and 100 µl of anti-human alkaline-phosphatase conjugate (Promega, Madison, Wis.) diluted 1/5000 in BLOTTO was added. After incubation for 1 hour at RT, the plates were then washed four times with TBS followed by incubation with a 1 mg/ml solution of p-nitrophenyl phosphate (PNPP). Substrate development was allowed to proceed for 30 to 45 minutes, then the absorbence of the wells at 405 nm was determined using a multiwell plate reader (Du Pont Co, Wilmington, Del.).

Figure 7:
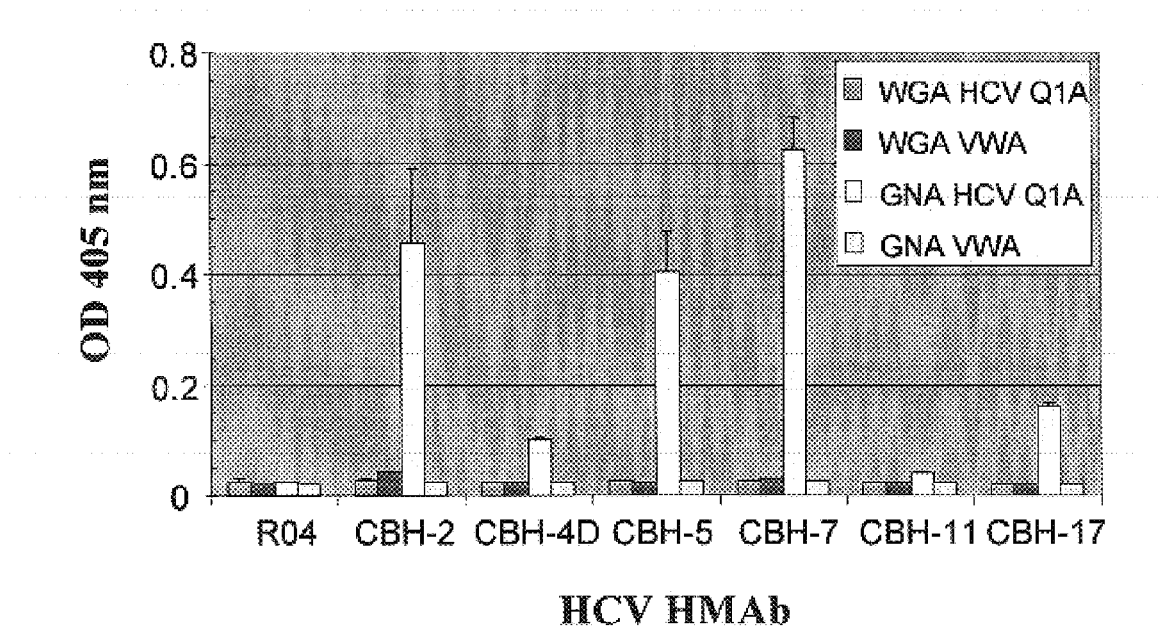

HCV 1a E2 produced by recombinant Q1a vaccinia virus was employed as a source of HCV E2 and six HCV HMAbs were employed as detection reagents (FIG. 7). No reactivity was observed to proteins captured with either lectin with a control monoclonal and only background levels of reactivity were observed for all HCV HMAbs with proteins captured by WGA. In contrast, HCV HMAbs CBH-2, CBH-5, CBH-7 all exhibited strong reactivity to proteins captured by GNA. Additionally HCV HMAbs CBH-17 and CBH-4D had lower levels of reactivity with GNA captured proteins. The HCV HMAb CBH-11 was not reactive with GNA captured proteins. This suggests that HCV HMAb CBH-11 does not recognize this particular E2. However it is clear that the GNA capture ELISA is extremely useful for analyzing the reactivity of HMAbs with HCV E2.

Figure 8:
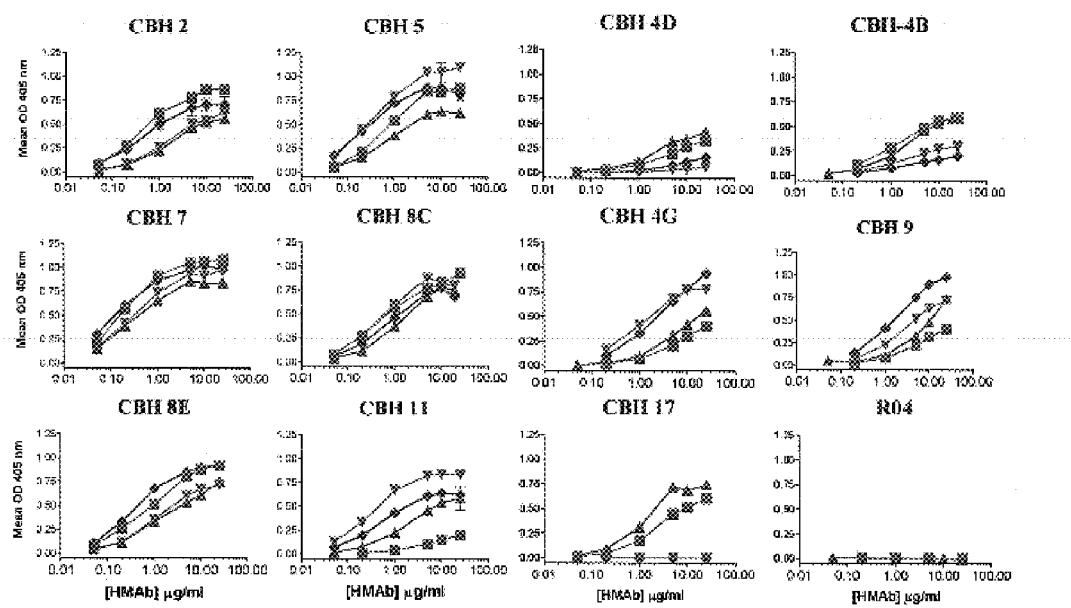

Therefore the reactivity of the HCV HMAbs was then evaluated with recombinant vaccinia virus expressing E2 proteins of divergent genotypes (FIG. 8). All 11 HCV HMabs bound to two or more of the HCV E2 constructs and no specific signal was obtained with a control HMAb (Panel marked R04). The HMAbs with the highest relative affinity and levels of reactivity to E2 proteins of all four genotypes were CBH-7 and CBH-8C followed by HMAbs CBH-5, -2 and -8E. HMAbs CBH-4G and CBH-9 exhibited significantly greater reactivity to HCV E2 proteins of genotypes 2a and 2b, while HMAb CBH-11 was markedly less reactive with Q1a E2 protein. HMAb CBH-17, and to a lesser extent CBH-4D and CBH-4B, exhibited preferential binding to E2 proteins of genotype 1a or 1b relative to E2 proteins of genotypes 2a or 2b. These variations were not a result of varying efficiencies of capture of the different E2 proteins since the maximum signals obtained with the different E2 proteins were very comparable in all experiments. These results were consistent with the results obtained in IFA with the same constructs (See Table 3, above). Seven antibodies, CBH-2, -4G, -5, -7, -8C, -8E, and -9 exhibited significant reactivity with all tested HCV E2 constructs and can be considered broadly reactive.

The reactivity of all tested HMAbs with at least two HCV genotypes suggested that the epitopes recognized by the HCV HMAbs would be highly conserved (See FIG. 9). It was of interest to determine whether the epitopes recognized by the HMAbs would be conformational or linear in nature. This was addressed directly by comparing the reactivity of the HCV HMAbs to both native and denatured HCV E2 proteins (See FIG. 9). As expected all 11 HCV HMAbs recognize HCV 1b E2. Treatment of HCV E2 by heating to 56° C. in the presence of 0.5% SDS and 5 mM dithiothreitol results in complete abrogation of reactivity for 10 of the 11 HCV HMAbs. The sole exception is HMAb CBH-17, which retains approximately 90% of its reactivity with the denatured E2 protein. Western Blot analysis of the HMAb CBH-17 confirmed it was weakly reactive with HCV envelope proteins expressed by vQ1a, or vQ1b (data not shown). No reactivity with Western blotted vQ1a was observed with any of the remaining 10 HMAbs (data not shown). Thus 10 of the 11 HCV HMAbs recognize conformational epitopes.

Figure 10:
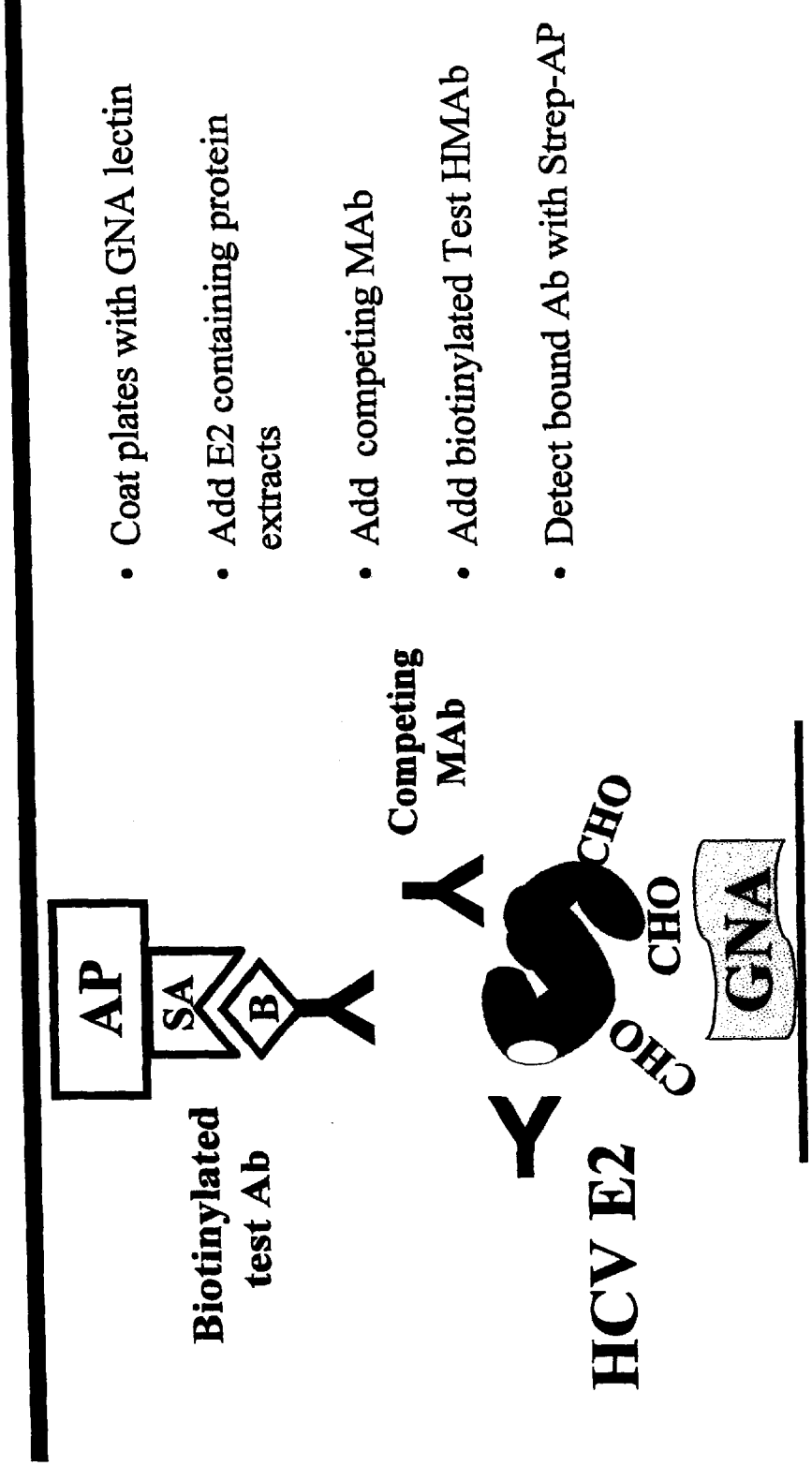
FIG. 10 depicts a schematic of the competition binding analysis employed in the experiments described in FIGS. 11, 12 and 13. GNA lectin is coated onto a solid surface and then added E2-containing protein extracts are captured by the lectin. Competing antibodies are allowed to bind to the captured E2 before removing unbound excess and adding labeled test antibody.
Figure 11:
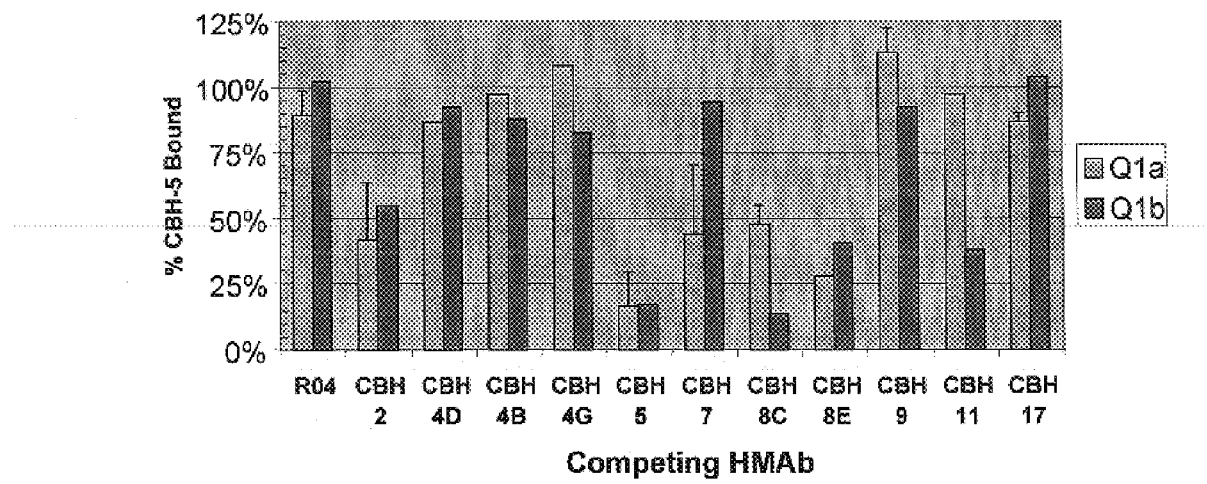
FIG. 11 is a bar graph of a competition analysis using HCV MNAb CBH-5. HCV E2 protein from cytoplasmic extracts of HeLa cells infected with vaccinia virus Q1a (blue bars) or Q1b (red bars) was captured with 500 ng of GNA. Bound HCV E2 was detected with 5 µg/ml of biotinylated CBH-5 in the presence of 25 µg/ml of the indicated HMAbs (x axis). Results are compared to binding of biotinylated CBH-5 in the absence of any competitor. Bars indicate the mean value obtained from replicate wells. Error bars indicate 1 standard deviation from the mean.

Lastly, competition analyses were employed to define which HCV HMAbs recognize the same (or very spatially close) epitopes. A schematic of this assay is depicted in FIG. 10. The HCV HMAbs CBH-5, CBH-2 or CBH-7 were biotinylated using standard methods and the reactivity of the biotinylated HMAbs to HCV type 1 or type 2 E2 in the presence of an excess of selected HMAbs was compared to those seen in samples without any added antibody. As seen in FIG. 11, the control HMAb R04 and the HCV HMAbs CBH-4D, -4B, -4G, -7, -9 and -17 all exhibited essentially no inhibition of HMAb CBH-5 binding. In contrast HMAb CBH-5 was inhibited 85% by an excess of itself and approximately 75% by HMAb CBH-8E. HMAb CBH-5 was inhibited more variably by HMAbs CBH-8C and CBH-11 and only inhibited to approximately 50% by HMAb CBH-2. In particular, the competition seen with HMAb CBH-2 is relatively equivocal, and it is not clear whether CBH-2 recognizes the same epitope as CHB-5 at a reduced affinity, or recognizes a separate spatially close epitope.

Figure 12:
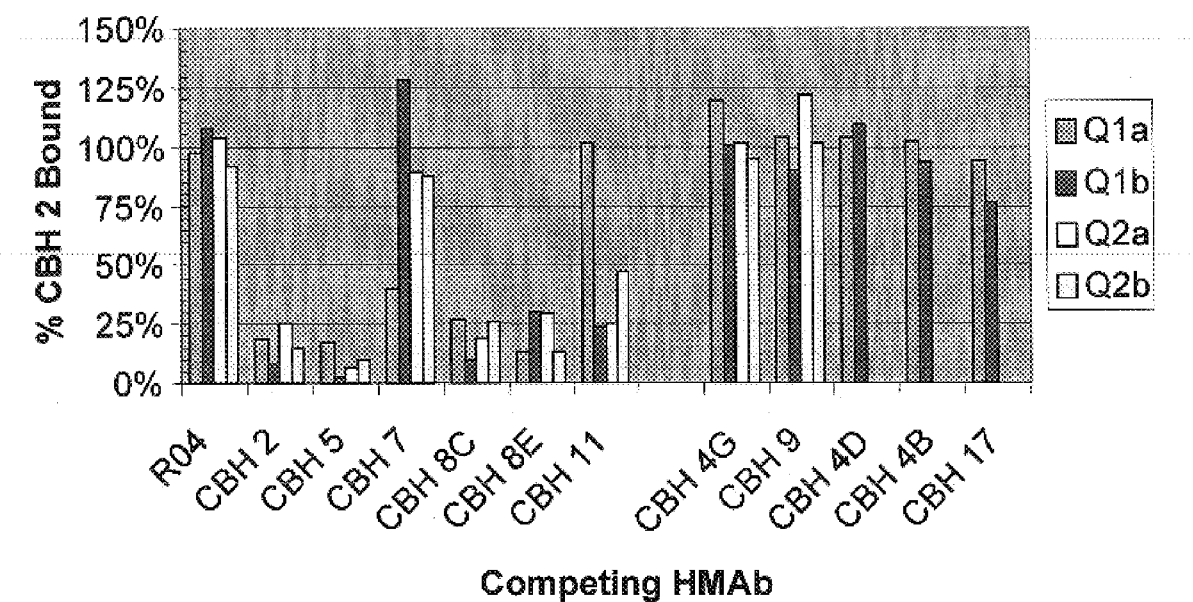
FIG. 12 is a competition analysis showing the ability of the HCV HMAbs to interfere with the binding of HMAb CBH-2 to HCV E2 proteins of multiple genotypes. HCV E2 protein from cytoplasmic extracts of HeLa cells infected with vaccinia virus Q1a (Blue bars), Q1b (red bars), Q2a (yellow bars) or Q2b (light blue bars) was captured with 500 ng of GNA lectin. The HMAbs CBH-4D, -4B, and -17 were only evaluated with HCV 1a or 1b E2 protein due to their limited reactivity to genotype 2 E2 proteins. Bound HCV E2 was detected with 2 µg/ml of biotinylated CBH-2 in the presence of 20 µg/ml of the indicated HMAbs (x axis). The bars indicate the binding observed in the presence of the indicated antibody relative to binding of biotinylated CBH-2 to HCV E2 in the absence of any competing antibody (y axis). R04 is a control HMAb that recognizes a cytomegalovirus protein. Bars indicate the mean value obtained from replicate wells. Error bars indicate one standard deviation from the mean.
Figure 13:
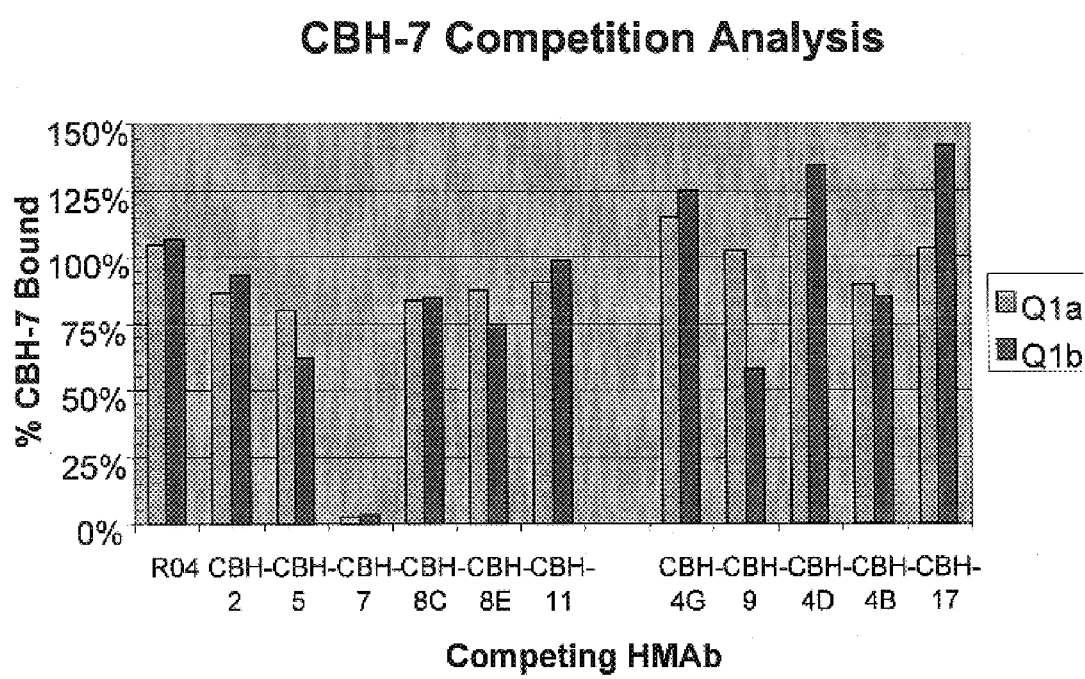
FIG. 13 is a competition analysis showing that HCV HMAb CBH-7 recognizes a unique epitope. HCV E2 protein from cytoplasmic extracts of HeLa cells infected with vaccinia virus Q1a (Blue bars) or Q1b (red bars) was captured with 500 ng of GNA lectin. Bound HCV E2 was detected with 2 µg/ml of biotinylated CBH-7 in the presence of 20 µg/ml of the indicated HMAbs (x axis). The bars indicate the binding observed in the presence of the indicated antibody relative to binding of biotinylated CBH-7 to HCV E2 in the absence of any competing antibody (y axis). R04 is a control HMAb that recognizes a cytomegalovirus protein. Bars indicate the mean value obtained from replicate wells. Error bars indicate one standard deviation from the mean.

Analysis of the antibody competition with HMAb. CBBH-2, (FIG. 12), indicated that HMAb CBH-2 binding was inhibited to be greater than 75% by itself and HMAbs CBH-5, -8C, and -8E. In contrast, CBH-7. inhibited binding to only Q1a proteins by 60%, and CBH-11 inhibited binding only to Q1b and Q2a proteins. As with HMAb CBH-5, no competition was observed with HMAbs CBH-4G, 4D, 4B, 9, or 17. Analysis of competition results with HMAb CBH-7 (FIG. 13) indicate that the only HMAb that significantly inhibited binding of CBH-7 was itself. These data demonstrate that among the broadly reactive HMAbs, CBH-2, -5, 11, and -7 all recognize distinct epitopes. The possibility remains that CBH-2, 8C, and 8E may recognize either the same epitope or two distinct epitopes. Additionally CBH-9, and CBH-4G may recognize the same epitope or two distinct epitopes, but their failure to compete with CBH-2, 5 etc ensures that they do not recognize the same epitope(s) as the other broadly reactive HMAbs. Thus, minimally the broadly reactive HMAbs recognize five distinct epitopes.

Example 5

Assessment of HMAb Activity in the Neutralization of Binding Assay

The neutralization of binding (NOB) assays tests whether a given antibody or serum can prevent the binding of HCV E2 protein to a putative receptor, expressed on human T cell lines. The NOB assays was performed using methods and HCV E2 proteins previously described Rosa, et al, supra; lshii, et al., supra. Briefly, 1 $\mu$g of the HCV E2 1a protein produced in mammalian cells Rosa, et al, supra was mixed with serial dilution of antibodies (from 0.1 to 300 $\mu$g/ml) and incubated for 30 min. at 37° C. Molt-4 cells ($10^5$) were added to the mixture and incubated on ice for 1 hour. After washing, the amount of HCV-E2 bound to Molt-4 cells was assessed by flow cytometry as described previously Rosa, et al., supra. The NOB titer is defined as the serum dilution that shows 50% neutralization of E2 binding.

The ability of HMAbs to inhibit binding of HCV 1a E2 to CD81 expressing target cells was assessed with the neutralization of binding (NOB) assay Rosa, et al., supra. HMAbs CBH-4D, 4B, 4G, and 17 did not block the binding of E2 to target cells at concentrations of less than 25 $\mu$g/ml. HMAbs CBH-2, 5, 7, 8C, 8E, and 11 achieved 50% inhibition of E2 binding at concentrations of 1 to 10 $\mu$g/ml in multiple experiments (Table 4).

Example 6

Effect of HCV HMAbs on E2 Binding to CD81: Microtiter Plate Assays

Figure 14:
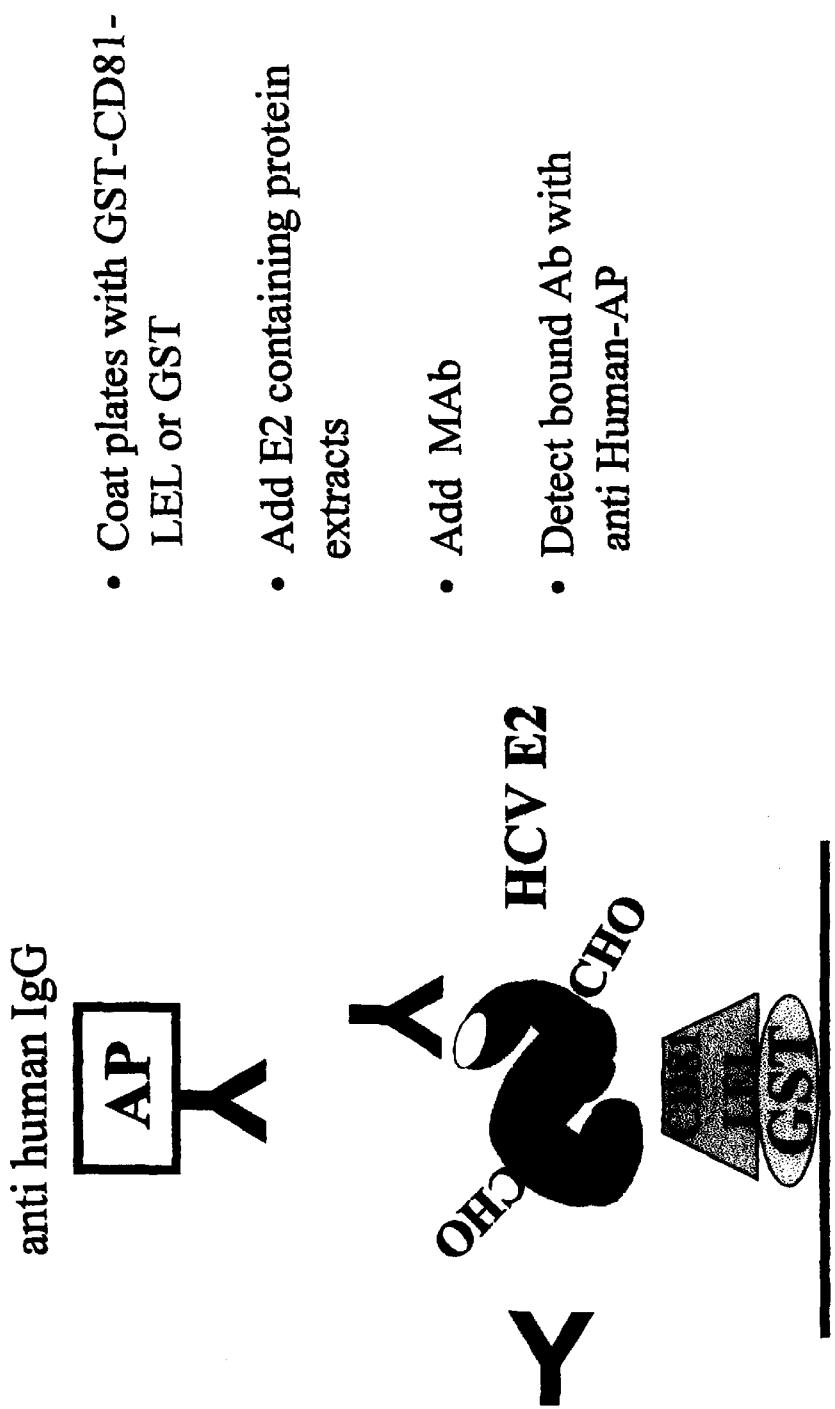
FIG. 14 depicts a schematic for assessing the ability of antibodies to block CD81 binding to E2 proteins as employed in the experiments described in FIG. 15. Recombinant CD81 is coated onto a solid surface. E2-containing protein extracts are then either added directly, or after preincubation with the test antibody. Bound test antibody-E2 complexes are detected using an appropriate labeled secondary antibody.

Recently, the human tetraspannin protein CD81 has been identified as a potential receptor for HCV and the cellular target protein for HCV E2 in the NOB assay. The binding site for HCV E2 within CD81 has been localized to the large extracellular loop, CD81-LEL (Pileri, et al., 1998 *Science* 282:938–941), previously referred to as extracellular loop 2 or LEL. To prevent confusion between E2 and LEL we have opted to refer to this region as the Large Extracellular Loop (LEL). The large extracellular loop of human CD81 (CD81-LEL) was expressed as a fusion protein with glutathione-S-transferase employing the pGEX vector (GST-2T). Construction and purification of the protein were as described Flint, et al., 1999 *J Virology* 73:6235–6244. This CD81-LEL-GST fusion protein was used to determine which HMAbs could recognize CD81-HCV E2 complexes. A schematic of this assay is provided in FIG. 14. Microtiter plate wells were coated with 100 ng of purified CD81-LEL or non-recombinant GST diluted in PBS. After 2 hours at 37° C, wells were washed one time with TBS and blocked by incubation with 150 μl of BLOTTO for 1 hour at RT. Extract from BSC 1 cells infected with HCV E2 expressing vaccinia virus was combined with test antibody in 100 μl of BLOTTO in coated plates that were incubated overnight with gentle agitation at 4° C. Wells were then washed three times with TBS followed by adding appropriate alkaline-phosphate conjugated secondary antibody and PNPP substrate as described in Example 4.

To confirm the NOB results using E2 proteins of multiple genotypes, we assessed whether the HCV HMAbs could inhibit the interaction of HCV E2 with CD81. Microtiter plates were first coated with purified CD81-LEL glutathione-S-transferase fusion protein to which an excess HCV E2 was added in the presence of the HCV HMAbs. Because HCV E2 binds specifically to human CD81 but not CD81 proteins of most other primates Rosa, et al., supra, the E2 proteins were produced in the green monkey kidney cell line BSC-1 to minimize the effect of endogenous CD81. Both anti-HCV and control antibodies were not captured by purified non-recombinant glutathione-S-transferase. Nor were the HCV or control antibodies captured by CD81 when combined with extracts of BSC-1 cells infected with wild type vaccinia virus (data not shown).

Figure 15:
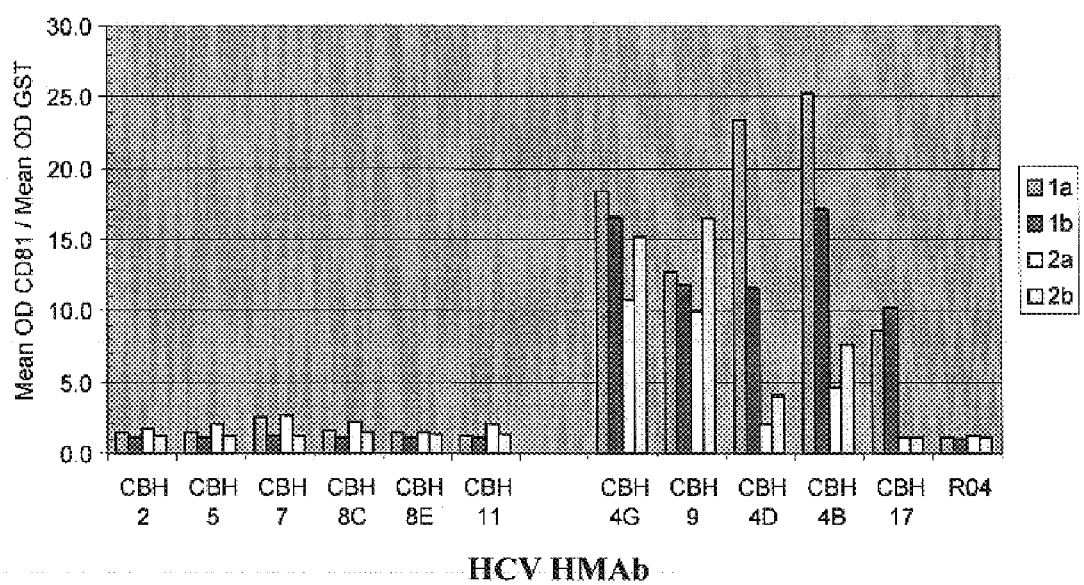
FIG. 15 shows that a bar graph that demonstrates that a subset of HCV HMAbs react with HCV E2 when bound to CD81-LEL. Extracts from BSC-1 cells infected with recombinant vaccinia virus expressing HCV E2 proteins were combined with 5 µg/ml of the indicated HMAbs (x axis) in a total volume of 100 µl and incubated in microtiter plate wells coated with 100 ng of a GST CD81-LEL fusion protein or non-recombinant GST overnight. Wells were washed and bound antibody was detected using an appropriate alkaline-phosphate conjugated secondary antibody and PNPP substrate as further described in Example 6 Values are the mean OD value of antibody captured by CD81 divided by the mean OD value for antibody captured by GST in the presence of 1a (purple bars),1b (red bars), 2a (yellow bars), or 2b (green bars) E2 protein. OD values obtained from wells coated with GST ranged between 0.021 and 0.081.

The NOB negative HMAb CBH-4G was captured onto CD81 coated plates to equivalent extents with E2 proteins of all four genotypes tested. The HMAbs CBH-4B, 4D and 17, were captured to variable extents onto CD81 coated plates by HCV 1a or 1b E2 proteins but not HCV 2a or 2b E2 proteins, consistent with the reactivity of these HMAbs with GNA captured E2 protein (FIG. 15). Titration analysis of the four NOB negative HMAbs confirmed that they all bound to HCV 1b E2 protein with 50% of maximum binding be obtained at concentrations between 1 and 10 μg/ml (Table 4). None of the NOB positive antibodies, CBH-2, 5, 7, 8C, 8E, and 11 were captured by CD81 with E2 proteins of any of the four genotypes tested (FIG. 15). Similar results were obtained when the HCV antibodies were added to wells on which HCV 1b E2 protein was already bound to CD81-LEL (data not shown) indicating that the results obtained were independent of each other of

TABLE 4

Inhibition of HCV E2-CD81 Binding by Anti-HCV HMAbs

| HMAb | NOB 1a[a] | CD81 1b E2[b] |
|---|---|---|
| CBH 2 | 5 μg/ml | — |
| CBH 5 | 2 μg/ml | — |
| CBH 7 | 7 μg/ml | — |
| CBH 8C | 10 μg/ml | — |
| CBH 8E | 8 μg/ml | — |
| CBH 11 | 3 μg/ml | — |

TABLE 4-continued

Inhibition of HCV E2-CD81 Binding by Anti-HCV HMAbs

| HMAb | NOB 1a[a] | CD81 1b E2[b] |
|---|---|---|
| CBH 4G | — | 3 μg/ml |
| CBH 9 | — | 1 μg/ml |
| CBH 4B | — | 0.4 μg/ml |
| CBH 4D | — | 2 μg/ml |
| CBH 17 | — | 3 μg/ml |
| R04 | — | — |

[a]HMAb reactivity in representative NOB assays are presented as μg/ml of antibody that results in 50% inhibition of E2 binding to CD81 expressing T cells. Antibodies were tested at concentrations that ranged from 0.1 to 300 μg/ml. (−) = negative.
[b]HMAb reactivity is presented as the concentration of antibody (in μg/ml) that results in 50% of maximum binding to E2 captured by GNA or E2 captured by a CD81-LEL. (−) = negative.

addition of the E2 protein and the HCV HMAbs. Titration analysis of HMAbs CBH-2 and 7, which are strongly reactive with GNA captured E2 but negative with CD81 bound E2, confirmed that these antibodies did not bind to CD81-LEL E2 complex at concentrations of up to 25 μg/ml (data not shown). Thus, six HMAbs inhibited the binding of HCV E2 of multiple genotypes to CD81-LEL.

Example 7

Effect of HCV HMAbs on HCV Virion Binding to CD81

The virion-CD81 binding assay was performed as previously described (Pileri, et al., 1998 *Science* 282:938–941). Briefly ¼" polystyrene beads (Pierce, Rockford Ill.) were coated overnight with 50 μg/ml of purified recombinant LEL-TRX protein Pileri, et al., supra in a citrate buffer pH 4.0 at room temperature and then blocked for one hour with 2% BSA in 50 mM Tris.Cl pH 8, 1 mM EDTA, 100 mM NaCl (TEN) buffer. Serum containing 5×10[5] HCV RNA genomes was diluted in 200 μl TEN buffer with 10 μg of purified monoclonal antibodies and incubated for one hour at 4° C. The diluted serum was then added to the coated beads and incubated at 37° C. for 1–2 hours. After removal of supernatant, each bead was washed five times with 15 ml TEN buffer and bound virus was extracted using a commercially available kit (Qiagen, Basel, Switzerland). Polymerase chain reaction mediated evaluation of the RNA copy number was performed using a Perkin Elmer ABI 7700 sequence detection system, as described Pileri, et al., supra.

Figure 16:
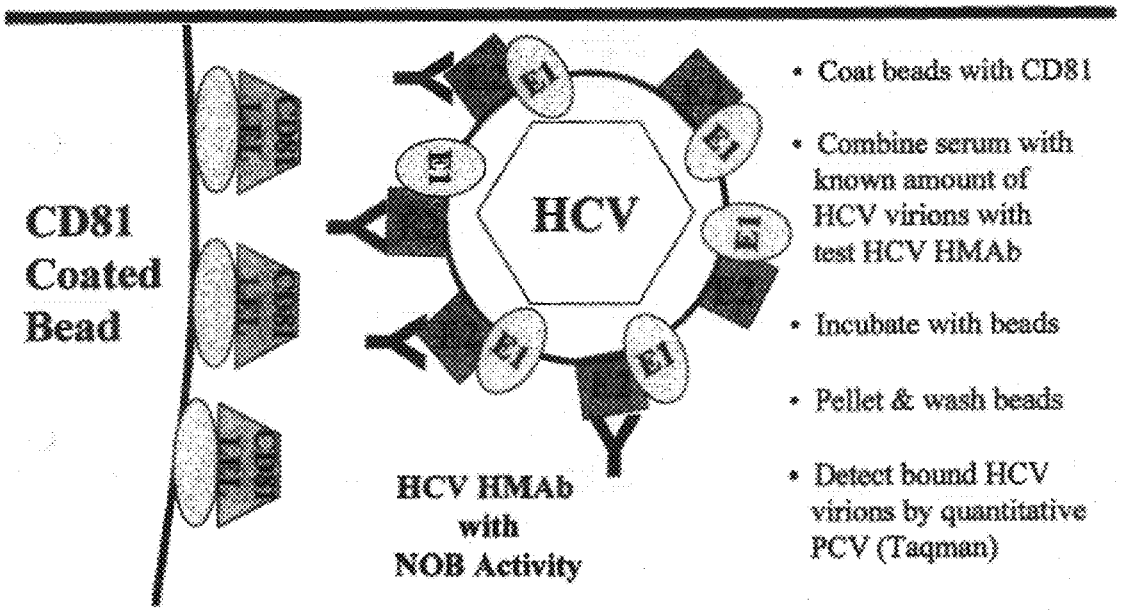
FIG. 16 depicts a schematic for assessing the ability of antibodies to block CD81 binding to HCV virions as employed in the experiments described in FIG. 17. Recombinant CD81 is coated onto a solid surface. HCV virions are preincubated with test antibodies, and then allowed to bind to immobilized CD81. Detection of bound HCV virions is measured by quantitative PCR.
Figure 17:
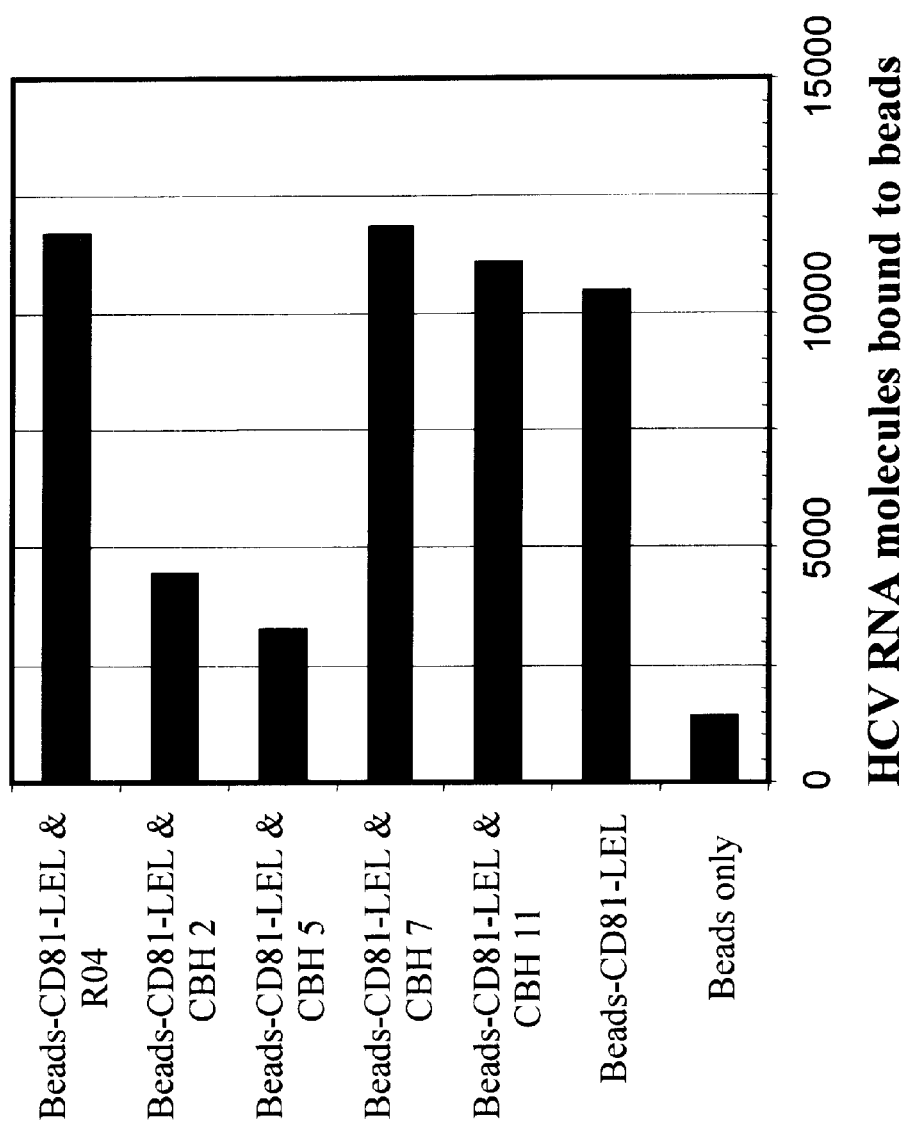
FIG. 17 shows that a bar graph demonstrates that HMAbs CBH-2 and CBH-5 inhibit binding of HCV virions to CD81. The number of HCV RNA molecules bound to polystyrene beads (x axis) after HCV 1a chimpanzee serum was combined with 10 µg of the indicated antibodies (y axis) and then allowed to bind to beads coated with CD81-LEL as described in Example 7.

Several of the HCV HMAbs that blocked recombinant E2 binding to CD81 were tested for the ability to interfere with the binding of HCV virions (including E1 and E2 protein expressed in a lipid bylayer) binding to CD81. Because of the lack of HCV culture assays in vitro, we took advantage of a PCR assay developed to demonstrate binding of envelope associated HCV RNA to CD81 Pileri, et al., supra. A schematic of this assay is depicted in FIG. 16. Briefly, the major extracellular loop of CD81 is attached to polystyrene beads and incubated with infectious plasma containing known amount of HCV 1a RNA molecules. After washing the amount of bead associated virus was measured by quantitative RT-PCR. The four NOB positive HMAbs with the highest apparent activity, HMAbs CBH-2, CBH-5, CBH-7, and CBH-11 were evaluated. No inhibition of virus binding was observed with a control antibody or with the NOB positive antibodies CBH-7 or CBH-11 In contrast, pre-incubation of infectious plasma with 10 μg/ml of HMAbs CBH-2 and CBH-5 inhibited HCV binding to CD81 (FIG. 17). These results support the view that these antibodies could bind HCV virions and may have a neutralizing effect in vivo.

Combining all of the results obtained in the above assays it is possible to construct a preliminary epitope assessment of the 11 HMAbs described herein. This is presented in Table 5. The epitope recognized by HMAb CBH-8C is separated from that recognized by HMAbs CBH-2 and /or CBH 8E by virtue of the very similar titrations obtained with CBH 8C with all four genotypes of HCV E2. CBH-2 and CBH-8E have the property of repeatedly exhibiting somewhat less reactivity with genotype 1b and 2b relative to values obtained with genotypes 2a and 1a. The assessment of the other distinct epitopes is very straightforward given the results obtained. However, it remains possible that additional experiments will serve to segregate the epitopes recognized; by CBH 4G and CBH 9 and /or the epitopes recognized by CBH :8E- and CBH-2.

Example 8

Microtiter Plate Assay for HCV Neutralizing Antibodies

To assist in the treatment and management of individuals with HCV infection, it would be desirable to know whether they have a potent antiviral immune response. Although several assays that can measure neutralizing antibody titers have been described, including the neutralization of binding assay described above and ex-vivo neutralization prior to inoculation of chimpanzees these assays are all cumbersome and are not suited to testing large numbers of samples. Therefore we employed HMAb CBH-4G which is equivalently reactive to HCV E2-CD81 complexes with E2 proteins of multiple genotypes in an inhibition assay to determine the level of neutralizing of binding like antibodies in human sera. Individual wells of microtiter plates were coated with either 500 ng of purified GNA lectin or 100 ng of GST-CD81-LEL fusion protein for one hour at 37° C. Wells were then washed one time with TBS and blocked for one hour with 150 µl of BLOTTO at room temperature. The wells are then washed one time with TBS and various dilutions of test sera or monoclonal antibodies were added to the appropriate wells in a total volume of 50 µl. At the same time 15 µl of HCV E2 protein containing extract was combined with 4 µg/ml of a biotinylated preparation of HMAb CBH-4G in a total volume of 50 µl of BLOTTO for each well. After incubation for 20 minutes at 4° C the E2 CBH-4G mixture was added to microtiter plate wells already containing the test antibody. The entire plate was then incubated overnight at 4° C. with gentle agitation. The next morning the contents of the wells were discarded and the wells washed three times with TBS. This was followed by the addition of 100 µl of strepavidin conjugated alkaline phosphatase (Amersham- Pharmacia, Piscataway N.J.) diluted 1/1000 in PBS plus 0.1% Tween-20 (Sigma, St Louis Mo.). The plates were then incubated for one hour at room temperature after which time the wells were washed four times with TBS and bound biotinylated antibody detected by incubation with PNPP substrate as described in examples 2 and above.

Figure 18:
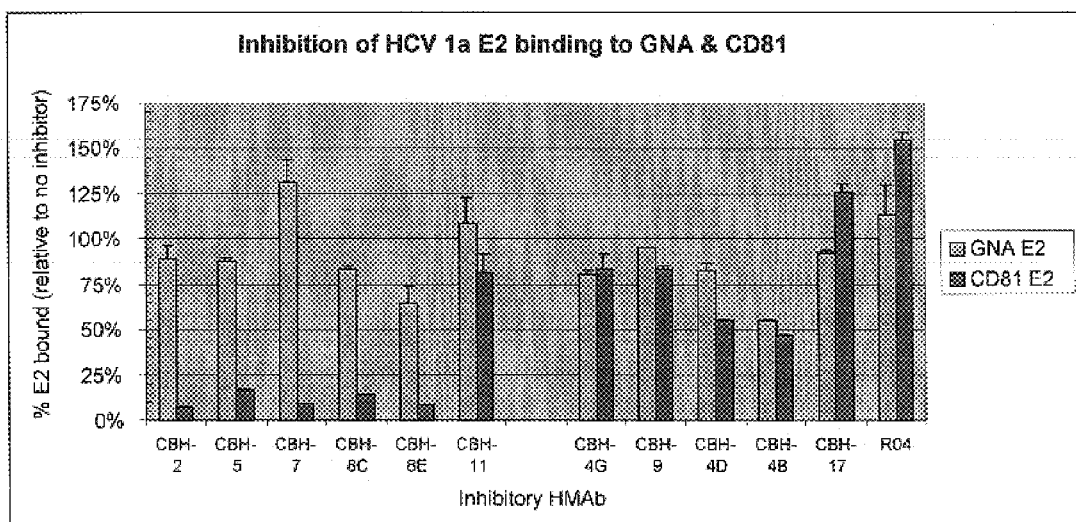
FIG. 18 is a bar graph that shows that HMAb CBH-4G can be employed to detect the presence of antibodies that inhibit binding of HCV E2 to CD81. HCV 1a E2 protein derived from extracts of BSC-1 cells infected with vaccinia virus Q1a was incubated with 4 µg/ml of a biotinylated preparation of HMAb CBH-4G for 20 minutes at 4° C. A 50 µl aliquot of the E2-CBH-4G complexes were then added to wells coated with either 500 ng of GNA (blue bars) or 100 ng of GST-CD81-LEL (red bars) to which 50 µl of a 40 µg/ml of the indicated antibodies (x axis) was added. R04 is a control HMAb that recognizes a cytomegalovirus protein. After an overnight incubation at 4° C the wells were washed and bound biotinylated CBH-4G detected as described in Example 8. The bars indicate the mean signal obtained from duplicate wells in the presence of the indicated antibody relative to the signal obtained in the absence of any competing antibody. Error bars indicate one standard deviation from the mean.

The results obtained when the panel of 11 HCV HMAbs was used as test antibodies are presented in FIG. 18. In this experiment the ability of a 20 µg/ml concentration of the HCV HMAbs to inhibit the binding of HCV genotype 1a E2 protein to human CD81 -LEL was evaluated. Inhibition-of binding observed in CD81-LEL coated wells are compared to results obtained with the same antibody in GNA lectin coated wells. Inhibition observed of E2 binding in GNA coated wells reflect inhibition of the interaction between the CBH-4G detection antibody and the competing antibody. Inhibition observed specifically in the CD81-LEL coated wells reflects inhibition of the interaction between CD81 and E2. None of the 11 HCV HMAbs or the control antibody, R04 exhibited more than 50% inhibition of CBH-4G binding to E2 captured by GNA. In contrast five of the six HCV HMAbs previously shown to be neutralization of binding positive strongly inhibited binding of CBH-4G-E2 complex to CD81-LEL. The lone exception was HMAb CBH-11, which does not efficiently recognize the Q1a isolate of genotype 1a E2 protein. The HMAbs CBH-4B, -4G, -4D, -9, and -17, which recognize CD81-LEL-E2 complexes all minimally effected binding of CBH-4G bound E2 to CD81 -LEL. Thus HMAb CBH-4G can effectively discriminate between antibodies that can or cannot inhibit the interaction of HCV E2 with CD81.

TABLE 5

Preliminary epitope analysis of HCV HMAbs

| Epitope | Type[1] | HMAb | Inhibits E2-CD81[2] | Binds to HCV Virion | Comp w CBH 2 | 1a | 1b | 2a | 2b |
|---|---|---|---|---|---|---|---|---|---|
| 1 | CONF | CBH 2 | + | + | + | + | + | + | + |
|  |  | CBH 8E | + | ND | + | + | + | + | + |
| 2 | CONF | CBH 5 | + | + | +/−[3] | + | + | + | + |
| 3 | CONF | CBH 7 | + | − | − | + | + | + | + |
| 4 | CONF | CBH 11 | + | − | + | − | + | + | + |
| 5 | CONF | CBH 8C | + | ND | + | + | + | + | + |
| 6 | CONF | CBH 4G | − | ND | − | + | + | + | + |
|  |  | CBH 9 | − | ND | − | + | + | + | + |
| 7 | CONF | CBH 4B | − | ND | − | + | + | − | − |
|  |  | CBH 4D | − | ND | − | + | + | − | − |
| 8 | LIN | CBH 17 | − | ND | − | + | + | − | − |

[1]CONF = recognizes a conformational epitope; LIN = recognizes a linear epitope
[2]Summarizes results obtained in NOB assay and CD81-E2 binding assays described above
[3]Non reciprocal partial competition is observed. CBH-2 inhibits binding of CBH-5 to HCV 1a or 1b E2 protein at a level of ~50%. CBH-5 inhibits binding of CBH-2 to HCV E2 of genotypes 1a, 1b, 2a, or 2b to ~80 %.

Figure 19:
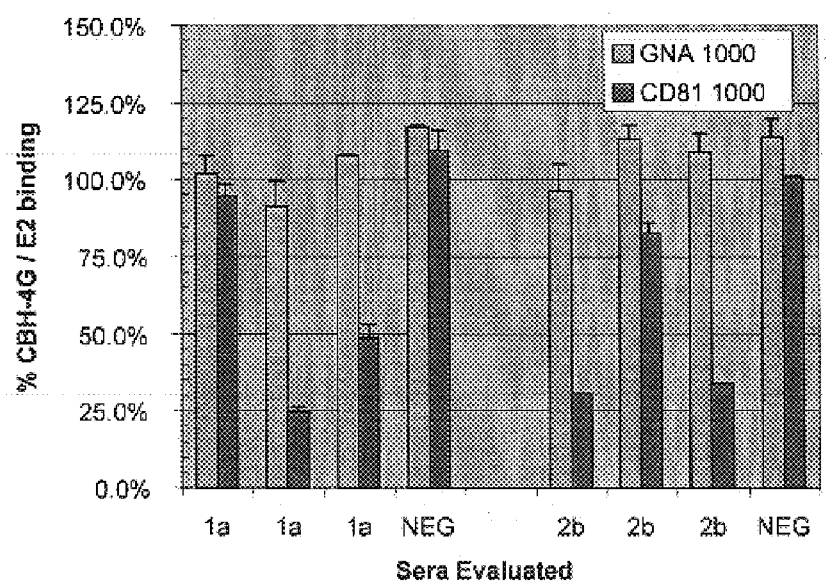
FIG. 19 is a bar graph that shows that HMAb CBH-4G can be employed to detect the presence of antibodies that inhibit binding of HCV E2 to CD81 in sera from HCV infected individuals. HCV 1a or 2b E2 protein derived from extracts of BSC-1 cells infected with vaccinia virus Q1a or Q2b was incubated with 4 µg/ml of a biotinylated preparation of HMAb CBH-4G for 20 minutes at 4° C. The four sera at left were tested with HCV 1a E2 protein; the four sera at right were tested with HCV 2b E2 protein. The E2-CBH-4G complexes were then added to wells coated with either 500 ng of GNA (blue bars) or 100 ng of GST-CD81-LEL (red bars) in the presence of a 1/500 dilution of the indicated sera from genotyped HCV infected (1a or 2b) or uninfected (NEG) individuals (x axis). After an overnight incubation at 4° C. the wells were washed and bound biotinylated CBH-4G detected as described in Example 8. The bars indicate the mean signal obtained from duplicate wells in the presence of the indicated serum (final dilution 1/1000) relative to the signal obtained in the absence of any competing serum. Error bars indicate one standard deviation from the mean.

Accordingly this experiment was then repeated using HCV and control sera in place of the HCV HMAbs (FIG. 19). Six genotyped HCV sera (three genotype 1a sera and three genotype 2b sera) and two HCV negative sera were tested against the homologous E2 protein at a dilution of 1/1000. As seen with the HCV HMAbs little or no inhibition of HCV E2 binding to GNA was observed. Nor did either of the negative sera significantly affect binding of HCV E2 to CD81-LEL. In contrast a wide variation of inhibition of E2 binding to CD81 -LEL was observed with the HCV Sera. Thus HMAb CBH-4G can be used to quantitative the level of antibodies capable of inhibiting HCV binding to a putative receptor, CD81, in a microtiter plate format.

It is evident from the above results that the monoclonal antibodies are an important addition in the development of diagnostics and therapies for the treatment of patients having HCV. By virtue of recognizing genotypes 1 and type 2, HCV assays can be performed with a higher expectancy of fewer false negatives and fewer antibodies are required for performing the assays to identify HCV infection. The antibodies will find use in a wide variety of protocols. In addition, the antibodies may be used to identify genotype, isolating virion particles, and identifying mimotopes. By virtue of their being human, they may be used in therapy, either prophylactic, to protect a subject who may be exposed to the virus, or therapeutic, to reduce the effective viral load of a patient.

---

What is claimed is:

1. A method for detecting HCV infection, the method comprising: providing a sample suspected of containing HCV; contacting the sample with an individual monoclonal antibody that binds to a conformational epitope found in an HCV envelope protein, which antibody is characterized by an ability to bind the epitope in envelope proteins from more than one HCV genotype; and detecting HCV infection by detecting the antibody bound to the conformational epitope, wherein the antibody is selected from the group consisting of CBH-2, CBH-4G, CBH-5, CBH-7, CBH-8C, and CBH-11, or binds to the same conformational epitopes as that bound by an antibody selected from the group consisting of CBH-2, CBH-4G, CBH-5, CBH-7, CBH-8C, and CBH-11.

2. A method for detecting HCV infection, the method comprising: providing a sample suspected of containing HCV; contacting the sample with an individual monoclonal antibody, which antibody is characterized by an ability to bind to at least one epitope in an envelope protein that is conformationally conserved between HCV genotype 1 and genotype 2; and detecting HCV infection by detecting the antibody bound to the at least one epitope in the envelope protein, wherein the antibody is selected from the group consisting of CBH-2, CBH-4G, CBH-5, CBH-7, CBH-8C, and CBH-11, or binds to the same conformational epitopes as that bound by an antibody selected from the group consisting of CBH-2, CBH-4G, CBH-5, CBH-7, CBH-8C, and CBH-11.

3. A human monoclonal antibody selected from the group consisting of CBH-2, -4D, -4B, -4G, -11, -5, -7, -8C, and -17.

4. A hybridoma which expresses a human monoclonal antibody selected from the group consisting of hybridomas expressing CBH-2 (ATCC PTA-4465), CBH-4D (ATCC PTA-4467), CBH-4B (ATCC PTA-4466), CBH-4G (ATCC PTA-4468), CBH-5 (ATCC PTA-4469), CBH-7 (ATCC PTA-4470), CBH-8C (ATCC PTA-4471), CBH-11 (ATTC PTA-4472), and CBH-17 (ATCC PTA-4473).

5. A hybridoma which expresses a human monoclonal antibody that binds to the same conformational epitopes as that bound by a human monoclonal antibody selected from the group consisting of CBH-2, CBH-4G, CBH-5, CBH-7, CBH-8C, and CBH-11, wherein the human monoclonal antibody binds to an epitope in envelope proteins from more than one HCV genotype.

6. A cell which expresses a human monoclonal antibody selected from the group consisting of hybridomas expressing CBH-2 (ATCC PTA-4465), CBH-4D (ATCC PTA-4467), CBH-4B (ATCC PTA-4466), CBH-4G (ATCC PTA-4468), CBH-5 PTA-4472), and CBH-17 (ATCC PTA-4473).

7. A cell which expresses a human monoclonal antibody that binds to the same conformational epitopes as that bound by a human monoclonal antibody selected from the group consisting of CBH-2, CBH-4G, CBH-5, CBH-7, and CBH- 8C, CBH-11, wherein the human monoclonal antibody binds to an epitope in envelope proteins from more than one HCV genotype.

8. A hybridoma which expresses a human monoclonal antibody that binds to the same conformational epitope, as that bound by a human monoclonal antibody selected from the group consisting of CBH-4D (ATCC PTA-4467), CBH-4B (ATCC PTA-4466), and CBH-17 (ATCC PTA-4473).

9. A cell which expresses a human monoclonal antibody that binds to the same conformational epitope as that bound by a human monoclonal antibody selected from the group consisting of CBH-4D (ATCC PTA-4467), CBH-4B (ATCC PTA-4466), and CBH-17 (ATCC PTA-4473).

* * * * *

UNITED STATES PATENT AND TRADEMARK OFFICE
CERTIFICATE OF CORRECTION

PATENT NO. : 6,692,908 B1
DATED : February 17, 2004
INVENTOR(S) : Foung et al.

It is certified that error appears in the above-identified patent and that said Letters Patent is hereby corrected as shown below:

Column 1,
Line 17, please delete "DA60596" and insert -- DA06596 -- therefor.

Signed and Sealed this

Twenty-eighth Day of December, 2004

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 6,692,908 B1 | Page 1 of 1 |
| APPLICATION NO. | : 09/430489 | |
| DATED | : February 17, 2004 | |
| INVENTOR(S) | : Foung et al. | |

It is certified that error appears in the above-identified patent and that said Letters Patent is hereby corrected as shown below:

In the Specification Under Column 1:

• Please replace Column 1, line no. 12-19 with:

-- FEDERALLY-SPONSORED RESEARCH OR DEVELOPMENT
 This invention was made with Government support under contracts AI047355, DA006596, and HL033811 awarded by the National Institutes of Health. The Government has certain rights in this invention. --

Signed and Sealed this

Thirteenth Day of March, 2012

David J. Kappos
*Director of the United States Patent and Trademark Office*

SEQUENCE LISTING

```
<160> NUMBER OF SEQ ID NOS: 27

<210> SEQ ID NO 1
<211> LENGTH: 160
<212> TYPE: DNA
<213> ORGANISM: Hepatitis C virus

<400> SEQUENCE: 1
ctcaactgga ttcaccaaag tgtgcggagc gcctccttgt gtcatcggag gggcgggcaa     60
caacaccctg cactgcccca ctgattgctt ccgcaagcat ccggacgcca catactctcg    120
gtgcggctcc ggtccctgga tcacacccag gtgcctggtc                          160

<210> SEQ ID NO 2
<211> LENGTH: 160
<212> TYPE: DNA
<213> ORGANISM: Hepatitis C virus

<400> SEQUENCE: 2
ctcaactgga ttcaccaaag tgtgcggagc gcccccctgt gtcatcggag gggcgggcaa     60
caacaccttg cgctgcccca ctgattgttt ccgcaagcat ccggaagcca cgtactctcg    120
gtgcggctcc ggtccctgga ttacgcccag gtgcctggtc                          160

<210> SEQ ID NO 3
<211> LENGTH: 160
<212> TYPE: DNA
<213> ORGANISM: Bovine Pancreatic Ribonuclease A

<400> SEQUENCE: 3
tagtactggg ttcactaaga cgtgcggagg ccccccgtgt aacatcgggg gggtcggtaa     60
ccgcaccttg atctgcccca cggactgctt ccggaagcac cccgaggcta cttacacaaa    120
atgtggctcg gggccctggt tgacacctag gtgcctagta                          160

<210> SEQ ID NO 4
<211> LENGTH: 160
<212> TYPE: DNA
<213> ORGANISM: T7 Bacteriophage

<400> SEQUENCE: 4
tggcacaggg ttcaccaaga cgtgtggggc ccccccatgt aacatcgggg gggtcggcaa     60
taacaccttg acttgcccca cggactgttt ccggaagcac cccgaggcca cttacaccaa    120
atgtggttcg gggccttggc tgacacctag gtgcatagtt                          160

<210> SEQ ID NO 5
<211> LENGTH: 166
```

<212> TYPE: DNA
<213> ORGANISM: Bacterial Protein

<400> SEQUENCE: 5
ctccactggc tacaccaaga cttgcggcgc accaccctgc cgcattagag ctgacttcaa    60
tgccagcatg gacttgttgt gccccacgga ctgttttagg aagcatcctg ataccaccta  120
catcaaatgt ggctctgggc cctggctcac gccaaggtgc ctgatc                 166

<210> SEQ ID NO 6
<211> LENGTH: 167
<212> TYPE: DNA
<213> ORGANISM: Artificial Sequence
<220> FEATURE:
<223> OTHER INFORMATION: Description of Artificial Sequence:Synthetic

<400> SEQUENCE: 6
ctccactgtt tcaccaaaac ttgcggcgca ccaccctgcc gcatcagagc tgactttaat    60
gccagcacgg acctgctgtg ccccacggac tgtttcagga agcatcctga agccacttac  120
atcaaatgtg gctctgggcc ccccctgtga cgccaaagtg cctaata                167

<210> SEQ ID NO 7
<211> LENGTH: 166
<212> TYPE: DNA
<213> ORGANISM: Artificial Sequence
<220> FEATURE:
<223> OTHER INFORMATION: Description of Artificial Sequence:synthetic

<400> SEQUENCE: 7
cgggactggg ttcactaaga catgcggtgc accaccttgc cgcattagga aagactacaa    60
cagcactatc gatttattgt gccccacaga ctgttttagg aagcacccag atgctaccta  120
tcttaagtgt ggagcagggc cttggttaac tcccaggtgc ctggta                166

<210> SEQ ID NO 8
<211> LENGTH: 166
<212> TYPE: DNA
<213> ORGANISM: Hepatitis C virus

<400> SEQUENCE: 8
tgggactggg ttcactaaga catgcggtgc accaccttgc cgcattagga gggactgcaa    60
cggaaccctc gacctattgt gccccacaga ctgtttcaga aagcacccag atactaccta  120
ccttaagtgt ggagcgggc cttggttgac ccccaaatgc atggta                  166

<210> SEQ ID NO 9
<211> LENGTH: 160
<212> TYPE: DNA
<213> ORGANISM: Hepatitis C virus

<400> SEQUENCE: 9
ctcaactgga ttcaccaaag tgtgcggagc gccccctgt gtcatcggag gggcgggcaa    60
caacaccttg cgctgcccca ctgattgttt ccgcaagcat ccggaagcca cgtactctcg  120
gtgcggctcc ggtccctgga ttacgcccag gtgcctggtc                        160

<210> SEQ ID NO 10
<211> LENGTH: 160
<212> TYPE: DNA
<213> ORGANISM: Hepatitis C virus

<400> SEQUENCE: 10

-continued

```
tggcacaggg ttcaccaaga cgtgtggggc cccccatgt aacatcgggg gggtcggcaa      60
taacaccttg acttgcccca cggactgttt ccggaagcac cccgaggcca cttacaccaa     120
atgtggttcg gggccttggc tgacacctag gtgcatagtt                           160
```

<210> SEQ ID NO 11
<211> LENGTH: 164
<212> TYPE: DNA
<213> ORGANISM: Hepatitis C virus

<400> SEQUENCE: 11

```
ctccactgtt tcaccaaaac ttgcggcgca ccaccctgcc gcatcagagc tgactttaat      60
gccagcacgg acctgctgtg ccccacggac tgtttcagga agcatcctga agccacttac    120
atcaaatgtg gctctgggcc cctgtgacgc caaagtgcct gata                     164
```

<210> SEQ ID NO 12
<211> LENGTH: 167
<212> TYPE: DNA
<213> ORGANISM: Artificial Sequence
<220> FEATURE:
<223> OTHER INFORMATION: Description of Artificial Sequence:Synthetic

<400> SEQUENCE: 12

```
tgggactggg ttcactaaga catgcggtgc accaccttgc cgcattagga gggactgcaa      60
cggaaccctc gacctattgt gccccacaga ctgtttcaga aagcacccag atactaccta    120
ccttaagtgt ggagcggggg ccttggttga ccccccaaatg catggta                  167
```

<210> SEQ ID NO 13
<211> LENGTH: 8
<212> TYPE: PRT
<213> ORGANISM: Hepatitis C virus

<400> SEQUENCE: 13

Asp Tyr Lys Asp Asp Asp Asp Lys
 1               5

<210> SEQ ID NO 14
<211> LENGTH: 10
<212> TYPE: PRT
<213> ORGANISM: Hepatitis C virus

<400> SEQUENCE: 14

Met Ala Ser Met Thr Gly Gly Gln Met Gly
 1               5                  10

<210> SEQ ID NO 15
<211> LENGTH: 15
<212> TYPE: PRT
<213> ORGANISM: Hepatitis C virus

<400> SEQUENCE: 15

Lys Glu Thr Ala Ala Ala Lys Phe Glu Arg Gln His Met Asp Ser
 1               5                  10                  15

<210> SEQ ID NO 16
<211> LENGTH: 20
<212> TYPE: DNA
<213> ORGANISM: Hepatitis C virus

<400> SEQUENCE: 16

```
cgcgcacraa gtasggyact                                                  20
```

<210> SEQ ID NO 17
<211> LENGTH: 21
<212> TYPE: DNA
<213> ORGANISM: Hepatitis C virus
<220> FEATURE:
<221> NAME/KEY: modified_base
<222> LOCATION: (9)
<223> OTHER INFORMATION: i

<400> SEQUENCE: 17
cgcatggcnt gggayatgat g                                        21

<210> SEQ ID NO 18
<211> LENGTH: 32
<212> TYPE: DNA
<213> ORGANISM: Hepatitis C virus

<400> SEQUENCE: 18
cgaagcttca tatgatcgct ggtgctcact gg                            32

<210> SEQ ID NO 19
<211> LENGTH: 38
<212> TYPE: DNA
<213> ORGANISM: Hepatitis C virus

<400> SEQUENCE: 19
gcggatccct gcagctacaa actggcttga agaatcca                      38

<210> SEQ ID NO 20
<211> LENGTH: 34
<212> TYPE: DNA
<213> ORGANISM: Hepatitis C virus

<400> SEQUENCE: 20
cgcatatgga gctcgcgggg gcccactggg gagt                          34

<210> SEQ ID NO 21
<211> LENGTH: 38
<212> TYPE: DNA
<213> ORGANISM: Hepatitis C virus

<400> SEQUENCE: 21
gctctagact gcagctatat gccagcctgg agcaccat                      38

<210> SEQ ID NO 22
<211> LENGTH: 34
<212> TYPE: DNA
<213> ORGANISM: Hepatitis C virus

<400> SEQUENCE: 22
cgctcgagcc atggttggcg gggctcattg gggc                          34

<210> SEQ ID NO 23
<211> LENGTH: 40
<212> TYPE: DNA
<213> ORGANISM: Hepatitis C virus

<400> SEQUENCE: 23
tcgaattcgg atcctacaaa gcaccttttta ggagataagc                   40

<210> SEQ ID NO 24
<211> LENGTH: 34
<212> TYPE: DNA
<213> ORGANISM: Hepatitis C virus

```
<400> SEQUENCE: 24
cgctcgagcc atggttttcg gcggccattg ggtg                              34

<210> SEQ ID NO 25
<211> LENGTH: 40
<212> TYPE: DNA
<213> ORGANISM: Hepatitis C virus

<400> SEQUENCE: 25
tcgaattcgg atcctacaga gacgctttaa ggaggtaggc                        40

<210> SEQ ID NO 26
<211> LENGTH: 23
<212> TYPE: DNA
<213> ORGANISM: Hepatitis C virus
<220> FEATURE:
<221> NAME/KEY: modified_base
<222> LOCATION: (15)
<223> OTHER INFORMATION: i

<400> SEQUENCE: 26
tggttcggbt gywcntggat gaa                                          23

<210> SEQ ID NO 27
<211> LENGTH: 26
<212> TYPE: DNA
<213> ORGANISM: Hepatitis C virus
<220> FEATURE:
<221> NAME/KEY: modified_base
<222> LOCATION: (9)
<223> OTHER INFORMATION: i
<221> NAME/KEY: modified_base
<222> LOCATION: (18)
<223> OTHER INFORMATION: i

<400> SEQUENCE: 27
taatgccana rcckrtangg gtagtc                                       26
```